United States Patent
Tojo et al.

(10) Patent No.: US 8,940,514 B2
(45) Date of Patent: Jan. 27, 2015

(54) THIOESTERASE AND A METHOD OF PRODUCING FATTY ACIDS OR LIPIDS USING THE THIOESTERASE

(75) Inventors: Takuto Tojo, Haga-gun (JP); Keiji Endo, Haga-gun (JP)

(73) Assignee: Kao Corporation, Tokyo (JP)

( * ) Notice: Subject to any disclaimer, the term of this patent is extended or adjusted under 35 U.S.C. 154(b) by 235 days.

(21) Appl. No.: 13/696,147

(22) PCT Filed: Apr. 13, 2011

(86) PCT No.: PCT/JP2011/059181
§ 371 (c)(1),
(2), (4) Date: Nov. 5, 2012

(87) PCT Pub. No.: WO2011/138891
PCT Pub. Date: Nov. 10, 2011

(65) Prior Publication Data
US 2013/0059351 A1    Mar. 7, 2013

(30) Foreign Application Priority Data

May 6, 2010  (JP) ................. 2010-106570
Feb. 2, 2011  (JP) ................. 2011-020737

(51) Int. Cl.
| | | |
|---|---|---|
| C12N 9/18 | (2006.01) |
| A01H 1/06 | (2006.01) |
| C12N 15/00 | (2006.01) |
| C12N 1/20 | (2006.01) |
| C12N 15/82 | (2006.01) |
| C12N 9/16 | (2006.01) |
| C12P 7/64 | (2006.01) |

(52) U.S. Cl.
CPC .............. *C12N 15/8247* (2013.01); *C12N 9/16* (2013.01); *C12P 7/6418* (2013.01); *C12P 7/6436* (2013.01); *C12Y 301/02014* (2013.01)
USPC ................. 435/197; 435/320.1; 435/252.3; 536/23.2; 800/276

(58) Field of Classification Search
USPC ............ 435/197, 252.3, 320.1; 536/23.2; 800/276
See application file for complete search history.

(56) References Cited

U.S. PATENT DOCUMENTS

| | | | |
|---|---|---|---|
| 5,110,728 A | 5/1992 | Kridl et al. |
| 5,298,421 A | 3/1994 | Davies et al. |
| 5,667,997 A | 9/1997 | Voelker et al. |
| 5,723,761 A | 3/1998 | Voelker et al. |
| 5,850,022 A | 12/1998 | Dehesh et al. |
| 5,925,805 A | 7/1999 | Ohlrogge et al. |
| 6,476,294 B1 | 11/2002 | Lassner et al. |
| 2004/0093638 A1 | 5/2004 | Sasaki et al. |

FOREIGN PATENT DOCUMENTS

| | | |
|---|---|---|
| EP | 1 298 214 A2 | 4/1991 |
| JP | 63-119680 A | 5/1988 |
| JP | 07-501924 A | 3/1995 |
| JP | 08-502892 A | 4/1996 |
| JP | 08-205863 A | 8/1996 |
| JP | 9-505470 A | 6/1997 |
| JP | 11-500902 A | 1/1999 |
| JP | 11-506323 A | 6/1999 |
| JP | 2002-524028 A | 8/2002 |
| JP | 2002-335786 A | 11/2002 |
| WO | WO 92/20236 | 11/1992 |
| WO | WO 94/10288 | 5/1994 |
| WO | WO 95/13390 | 5/1995 |
| WO | WO 96/23892 A3 | 8/1996 |
| WO | WO 96/38573 A1 | 12/1996 |
| WO | WO 00/05385 | 2/2000 |
| WO | WO 00/36114 A1 | 6/2000 |
| WO | WO 2008/076377 A2 | 6/2008 |

OTHER PUBLICATIONS

International Search Report (ISR) for PCT/JP2011/059181, I.A. fd: Apr. 13, 2011, mailed May 24, 2011 from the Japanese Patent Office, Tokyo, Japan.
International Preliminary Report on Patentability (IPRP), Chapter I of the Patent Cooperation Treaty, including the Written Opinion for PCT/JP2011/059181, I.A. fd; Apr. 13, 2011, issued Dec. 10, 2012, from the International Bureau of WIPO, Geneva, Switzerland.
Madoka, Y, et al., "Chloroplast Transformation with Modified accD Operon Increases Acetyl-CoA Carboxylase and Causes Extension of Leaf Longevity and Increase in Seed Yield in Tobacco", Plant Cell Physiol., Dec. 2002; 43: 1518-1525, Japanese Society of Plant Physiologists, Kyoto, Japan.
Zou, J. et al.,"Modification of Seed Oil Content and Acyl Composition in the Brassicaceae by Expression of a Yeast sn-2 Acyltransferase Gene", Plant Cell, Jun. 1997; 9: 909-923, American Society of Plant Physiologists, Rockville, MD.
Jako, C, et al., "Seed-Specific Over-Expression of an Arabidopsis cDNA Encoding a Diacylglycerol Acyltransferase Enhances Seed Oil Content and Seed Weight", Plant Physiology, Jun. 2001; 126: 861-874, American Society of Plant Physiologists, Rockville, MD.
Voelker, TA, et al., "Fatty acid biosynthesis redirected to medium chains in transgenic oilseed plants", Science, Jul. 1992; 257: 72-74, Am. Assoc. Adv. Science, Washington, DC.
Yuan, L, et al., "Modification of the substrate specificity of an acyl-acyl carrier protein thioesterase by protein engineering", Proc. Natl. Acad. Sci. USA, Nov. 1995; 92; 10639-10643, National Academy of Sciences, Washington, DC.

*Primary Examiner* — Maryam Monshipouri
(74) *Attorney, Agent, or Firm* — Sterne, Kessler, Goldstein & Fox P.L.L.C.

(57) ABSTRACT

A thioesterase comprising an amino acid sequence set forth in SEQ ID NO: 1, a thioesterase gene encoding the thioesterase, a transformant comprising the gene, and a method of producing fatty acids or lipids using the transformant.

15 Claims, 3 Drawing Sheets

(a) Fatty acid composition in the Cocos nucifera L. endosperm (b) Fatty acid composition in the transformant having CTE gene

SEQUENCE LISTING

```
<160> NUMBER OF SEQ ID NOS: 37

<210> SEQ ID NO 1
<211> LENGTH: 303
<212> TYPE: PRT
<213> ORGANISM: Cocos nucifera

<400> SEQUENCE: 1

Leu Asp Ser Lys Lys Arg Gly Ala Asp Ala Val Ala Asp Ala Ser Gly
1               5                   10                  15
```

Val Gly Lys Met Val Lys Asn Gly Leu Val Tyr Arg Gln Asn Phe Ser
                20                  25                  30

Ile Arg Ser Tyr Glu Ile Gly Val Asp Lys Arg Ala Ser Val Glu Ala
            35                  40                  45

Leu Met Asn His Phe Gln Glu Thr Ser Leu Asn His Cys Lys Cys Ile
 50                  55                  60

Gly Leu Met His Gly Gly Phe Gly Cys Thr Pro Glu Met Thr Arg Arg
 65                  70                  75                  80

Asn Leu Ile Trp Val Val Ala Lys Met Leu Val His Val Glu Arg Tyr
                85                  90                  95

Pro Trp Trp Gly Asp Val Val Gln Ile Asn Thr Trp Ile Ser Ser Ser
            100                 105                 110

Gly Lys Asn Gly Met Gly Arg Asp Trp His Val His Asp Cys Gln Thr
        115                 120                 125

Gly Leu Pro Ile Met Arg Gly Thr Ser Val Trp Val Met Met Asp Lys
130                 135                 140

His Thr Arg Arg Leu Ser Lys Leu Pro Glu Glu Val Arg Ala Glu Ile
145                 150                 155                 160

Thr Pro Phe Phe Ser Glu Arg Asp Ala Val Leu Asp Asp Asn Gly Arg
                165                 170                 175

Lys Leu Pro Lys Phe Asp Asp Asp Ser Ala Ala His Val Arg Arg Gly
            180                 185                 190

Leu Thr Pro Arg Trp His Asp Phe Asp Val Asn Gln His Val Asn Asn
        195                 200                 205

Val Lys Tyr Val Gly Trp Ile Leu Glu Ser Val Pro Val Trp Met Leu
210                 215                 220

Asp Gly Tyr Glu Val Ala Thr Met Ser Leu Glu Tyr Arg Arg Glu Cys
225                 230                 235                 240

Arg Met Asp Ser Val Val Gln Ser Leu Thr Ala Val Ser Ser Asp His
                245                 250                 255

Ala Asp Gly Ser Pro Ile Val Cys Gln His Leu Leu Arg Leu Glu Asp
            260                 265                 270

Gly Thr Glu Ile Val Arg Gly Gln Thr Glu Trp Arg Pro Lys Gln Gln
        275                 280                 285

Ala Cys Asp Leu Gly Asn Met Gly Leu His Pro Thr Glu Ser Lys
290                 295                 300

<210> SEQ ID NO 2
<211> LENGTH: 912
<212> TYPE: DNA
<213> ORGANISM: Cocos nucifera

<400> SEQUENCE: 2
ctcgattcca agaagagggg ggccgacgcg gtcgcagatg cctctggggt cgggaagatg      60
gtcaagaatg gacttgttta caggcagaat ttttctatcc ggtcctacga aatcggggtt     120
gataaacgtg cttcggtaga ggcattgatg aatcatttcc aggaaacgtc gcttaaccat     180
tgcaagtgta ttggccttat gcatggcggc tttggttgta caccagagat gactcgaaga     240
aatctgatat gggttgttgc caaaatgctg gttcatgtcg aacgttatcc ttggtgggga     300
gacgtggttc aaataaatac gtggattagt tcatctggaa agaatggtat gggacgtgat     360
tggcatgttc atgactgcca aactggccta cctattatga ggggtaccag tgtctgggtc     420
atgatggata acacacgag gagactgtct aaacttcctg aagaagttag agcagagata     480 accccttct tttcagagcg tgatgctgtt ttggacgata acggcagaaa acttcccaag     540

```
ttcgatgatg attctgcagc tcatgttcga aggggcttga ctcctcgttg gcatgatttc    600
gatgtaaatc agcatgtgaa caatgtcaaa tacgtcggct ggattcttga gagcgttcct    660
gtgtggatgt tggatggcta cgaggttgca accatgagtc tggaataccg gagggagtgt    720
aggatggata tgtggtgca gtctctcacc gccgtctctt ccgaccacgc cgacggctcc    780
cccatcgtgt gccagcatct tctgcggctc gaggatggga ctgagattgt gaggggtcaa    840
acagaatgga ggcctaagca gcaggcttgt gatcttggga acatgggtct gcacccaact    900
gagagtaaat ga                                                         912
```

<210> SEQ ID NO 3
<211> LENGTH: 299
<212> TYPE: PRT
<213> ORGANISM: Umbellularia californica

<400> SEQUENCE: 3

```
Leu Glu Trp Lys Pro Lys Pro Lys Leu Pro Gln Leu Leu Asp Asp His
  1               5                  10                  15

Phe Gly Leu His Gly Leu Val Phe Arg Arg Thr Phe Ala Ile Arg Ser
                 20                  25                  30

Tyr Glu Val Gly Pro Asp Arg Ser Thr Ser Ile Leu Ala Val Met Asn
             35                  40                  45

His Met Gln Glu Ala Thr Leu Asn His Ala Lys Ser Val Gly Ile Leu
         50                  55                  60

Gly Asp Gly Phe Gly Thr Thr Leu Glu Met Ser Lys Arg Asp Leu Met
 65                  70                  75                  80

Trp Val Val Arg Arg Thr His Val Ala Val Glu Arg Tyr Pro Thr Trp
                 85                  90                  95

Gly Asp Thr Val Glu Val Glu Cys Trp Ile Gly Ala Ser Gly Asn Asn
            100                 105                 110

Gly Met Arg Arg Asp Phe Leu Val Arg Asp Cys Lys Thr Gly Glu Ile
        115                 120                 125

Leu Thr Arg Cys Thr Ser Leu Ser Val Leu Met Asn Thr Arg Thr Arg
130                 135                 140

Arg Leu Ser Thr Ile Pro Asp Glu Val Arg Gly Glu Ile Gly Pro Ala
145                 150                 155                 160

Phe Ile Asp Asn Val Ala Val Lys Asp Asp Glu Ile Lys Lys Leu Gln
                165                 170                 175

Lys Leu Asn Asp Ser Thr Ala Asp Tyr Ile Gln Gly Gly Leu Thr Pro
            180                 185                 190

Arg Trp Asn Asp Leu Asp Val Asn Gln His Val Asn Asn Leu Lys Tyr
        195                 200                 205

Val Ala Trp Val Phe Glu Thr Val Pro Asp Ser Ile Phe Glu Ser His
    210                 215                 220

His Ile Ser Ser Phe Thr Leu Glu Tyr Arg Arg Glu Cys Thr Arg Asp
225                 230                 235                 240

Ser Val Leu Arg Ser Leu Thr Thr Val Ser Gly Gly Ser Ser Glu Ala
                245                 250                 255

Gly Leu Val Cys Asp His Leu Leu Gln Leu Glu Gly Gly Ser Glu Val
            260                 265                 270

Leu Arg Ala Arg Thr Glu Trp Arg Pro Lys Leu Thr Asp Ser Phe Arg
        275                 280                 285

Gly Ile Ser Val Ile Pro Ala Glu Pro Arg Val
    290                 295
```

<210> SEQ ID NO 4
<211> LENGTH: 901
<212> TYPE: DNA
<213> ORGANISM: Umbellularia californica

<400> SEQUENCE: 4

```
tctagagtgg aagccgaagc cgaagctacc ccagttgctt gatgaccatt ttggactgca      60
tgggttagtt ttcaggcgca cctttgccat cagatcttat gaggtgggac ctgaccgctc     120
cacatctata ctggctgtta tgaatcacat gcaggaggct acacttaatc atgcgaagag     180
tgtgggaatt ctaggagatg gattcgggac gacgctagag atgagtaaga gagatctgat     240
gtgggttgtg agacgcacgc atgttgctgt ggaacggtac cctacttggg gtgatactgt     300
agaagtagag tgctggattg gtgcatctgg aaataatggc atgcgacgtg atttccttgt     360
ccgggactgc aaaacaggcg aaattcttac aagatgtacc agcctttcgg tgctgatgaa     420
tacaaggaca aggaggttgt ccacaatccc tgacgaagtt agaggggaga tagggcctgc     480
attcattgat aatgtggctg tcaaggacga tgaaattaag aaactacaga agctcaatga     540
cagcactgca gattacatcc aaggaggttt gactcctcga tggaatgatt tggatgtcaa     600
tcagcatgtg aacaacctca aatacgttgc ctgggttttt gagaccgtcc cagactccat     660
ctttgagagt catcatattt ccagcttcac tcttgaatac aggagagagt gcacgaggga     720
tagcgtgctg cggtccctga ccactgtctc tggtggctcg tcggaggctg ggttagtgtg     780
cgatcacttg ctccagcttg aaggtgggtc tgaggtattg agggcaagaa cagagtggag     840
gcctaagctt accgatagtt tcagagggat tagtgtgata cccgcagaac cgagggtgta     900
a                                                                    901
```

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide Primer No. 1
<220> FEATURE:
<221> NAME/KEY: misc_feature
<222> LOCATION: (15)..(15)
<223> OTHER INFORMATION: The symbol "n" represents i (inosine)
<220> FEATURE:
<221> NAME/KEY: misc_feature
<222> LOCATION: (18)..(18)
<223> OTHER INFORMATION: The symbol "n" represents i (inosine)

<400> SEQUENCE: 5

```
ttyathaayc arytnccnga ytgg                                             24
```

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide Primer No.2
<220> FEATURE:
<221> NAME/KEY: misc_feature
<222> LOCATION: (3)..(3)
<223> OTHER INFORMATION: The symbol "n" represents i (inosine)
<220> FEATURE:
<221> NAME/KEY: misc_feature
<222> LOCATION: (6)..(6)
<223> OTHER INFORMATION: The symbol "n" represents i (inosine)

<400> SEQUENCE: 6
gcngcngara arcartgg                                                         18

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide Primer No.3
<220> FEATURE:
<221> NAME/KEY: misc_feature
<222> LOCATION: (7)..(7)
<223> OTHER INFORMATION: The symbol "n" represents i (inosine)
<220> FEATURE:
<221> NAME/KEY: misc_feature
<222> LOCATION: (16)..(16)
<223> OTHER INFORMATION: The symbol "n" represents i (inosine)

<400> SEQUENCE: 7
rtayttnacr ttrttnacrt gytgrtt                                               27

<210> SEQ ID NO 8
<211> LENGTH: 15
<212> TYPE: DNA
<213> ORGANISM: Artificial Sequence
<220> FEATURE:
<223> OTHER INFORMATION: Oligonucleotide Primer No.4
<220> FEATURE:
<221> NAME/KEY: misc_feature
<222> LOCATION: (10)..(10)
<223> OTHER INFORMATION: The symbol "n" represents i (inosine)

<400> SEQUENCE: 8
rttcatcatn accca                                                            15

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide Primer No.5
<220> FEATURE:
<221> NAME/KEY: misc_feature
<222> LOCATION: (12)..(12)
<223> OTHER INFORMATION: The symbol "n" represents i (inosine)
<220> FEATURE:
<221> NAME/KEY: misc_feature
<222> LOCATION: (18)..(18)
<223> OTHER INFORMATION: The symbol "n" represents i (inosine)

<400> SEQUENCE: 9
acrtgytgrt tnacrtcnar rtc                                                   23

<210> SEQ ID NO 10
<211> LENGTH: 20
<212> TYPE: DNA
<213> ORGANISM: Artificial
<220> FEATURE:
<223> OTHER INFORMATION: Oligonucleotide Primer No.6

<400> SEQUENCE: 10
cagtggaccc tgctcgattc                                                       20

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide Primer No.7

<400> SEQUENCE: 11

```
tttttttttt tttttttttt ttttt                                              25

<210> SEQ ID NO 12
<211> LENGTH: 39
<212> TYPE: DNA
<213> ORGANISM: Artificial Sequence
<220> FEATURE:
<223> OTHER INFORMATION: Oligonucleotide Primer No.8

<400> SEQUENCE: 12
caggtcgact ctagagctcg attccaagaa gagggggc                                39

<210> SEQ ID NO 13
<211> LENGTH: 33
<212> TYPE: DNA
<213> ORGANISM: Artificial Sequence
<220> FEATURE:
<223> OTHER INFORMATION: Oligonucleotide Primer No.9

<400> SEQUENCE: 13
ggtacccggg gatcctcatt tactctcagt tgg                                     33

<210> SEQ ID NO 14
<211> LENGTH: 24
<212> TYPE: DNA
<213> ORGANISM: Artificial Sequence
<220> FEATURE:
<223> OTHER INFORMATION: Oligonucleotide Primer No.10

<400> SEQUENCE: 14
ggatccccgg gtaccgagct cgaa                                               24

<210> SEQ ID NO 15
<211> LENGTH: 26
<212> TYPE: DNA
<213> ORGANISM: Artificial Sequence
<220> FEATURE:
<223> OTHER INFORMATION: Oligonucleotide Primer No.11

<400> SEQUENCE: 15
tctagagtcg acctgcaggc atgcaa                                             26

<210> SEQ ID NO 16
<211> LENGTH: 39
<212> TYPE: DNA
<213> ORGANISM: Artificial Sequence
<220> FEATURE:
<223> OTHER INFORMATION: Oligonucleotide Primer No.12

<400> SEQUENCE: 16
gcaggtcgac tctagagtgg aagccgaagc cgaagctac                               39

<210> SEQ ID NO 17
<211> LENGTH: 35
<212> TYPE: DNA
<213> ORGANISM: Artificial Sequence
<220> FEATURE:
<223> OTHER INFORMATION: Oligonucleotide Primer No.13

<400> SEQUENCE: 17
tcggtacccg gggatccctg cagcttctaa aaagt                                   35

<210> SEQ ID NO 18
<211> LENGTH: 1747
<212> TYPE: DNA
```

<213> ORGANISM: Brassica rapa

<400> SEQUENCE: 18

```
gatatcacta caatgtcgga gagacaaggc tgcgccagca tatacaaaag ggaaatgaag     60
atggccttt  gattagctgt gtagcatcag cagctaatct ctgggctctc atcatggatg    120
ctggaactgg attcacttct caagtttatg agttgtcacc ggtcttccta cacaaggtaa    180
taatcagttg aagcaattaa gaatcaattt gatttgtagt aaactaagaa gaacttacct    240
tatgttttcc ccgcaggact ggattatgga acaatgggaa agaactact  atataagctc    300
catagctggt tcagataacg ggagctcttt agttgttatg tcaaaaggtt agtgtttagt    360
gaataataaa cttataccac aaagtcttca ttgacttatt tatatacttg ttgtgaattg    420
ctaggaacta cttattctca gcagtcatac aaagtgagtg actcatttcc gttcaagtgg    480
ataaataaga aatggaaaga agattttcat gtaacctcca tgacaactgc tggtaatcgt    540
tggggtgtgg taatgtcgag gaactctggc ttctctgatc aggtaggttt ttgtctctta    600
tggtctgggg gttttttattt cccctgatag tctaatatga taaactctgc gttgtgaaag    660
gtggtggagc ttgacttttt gtacccaagc gatgggatac ataggaggtg ggagaatggg    720
tatagaataa catcaatggc agcaactgcg gatcaagcag cttttcatatt aagcatacca    780
aagcgtaaga tggtggatga aactcaagag actctccgca ccaccgcctt tccaagtact    840
catgtcaagg ttggttttctt tagctttgaa cacagatttg gatcttttttg ttttgtttcc    900
atatacttag gacctgagag cttttggttg atttttttt  caggacaaat gggcgaagaa    960
tctgtacatt gcatcaatat gctatggcag gacagtgtgc tgatacacac ttaagcatca   1020
tgtggaaagc caaagacaat tggagcgaga ctcagggtcg tcataatacc aatcaaagac   1080
gtaaaaccag acgcaacctc tttggttgaa tgtaatgaaa gggatgtgtc ttggtatgta   1140
tgtacgaata caaaagaga agatggaatt agtagtagaa atatttggga gcttttttaag   1200
ccttcaagt  gtgctttta  tcttattgat atcatccatt gcgttgtt  aatgcgtctc    1260
tagatatgtt cctatatctt tctcagtgtc tgataagtga atgtgagaa accataccga    1320
aaccaaaata ttcaaatctt attttttaata atgttgaatc actcggagtt gccaccttct   1380
gtgccaattg tgctgaatct atcacactag aaaaaaacat ttcttcaagg taatgacttg    1440
tggactatgt tctgaattct cattaagttt ttatttttctg aagtttaagt ttttacccttc   1500
tgttttgaaa tatatcgttc ataagatgtc acgccaggac atgagctaca catcgcacat    1560
agcatgcaga tcaggacgat ttgtcactca cttcaaacac ctaagagctt ctctctcaca    1620
gcgcacacac atatgcatgc aatatttaca cgtgatcgcc atgcaaatct ccattctcac    1680
ctataaatta gagcctcggc ttcactcttt actcaaacca aaactcatca ctacagaaca    1740
tacacaa                                                             1747
```

<210> SEQ ID NO 19
<211> LENGTH: 1255
<212> TYPE: DNA
<213> ORGANISM: Brassica rapa

<400> SEQUENCE: 19

```
gtgtgtatac cacggtgata tgagtgtggt tgttgatgta tgttaacact acatagtcat     60
ggtgtgtgtt ccataaaataa tgtactaatg taataagaac tactccgtag acggtaataa    120
aagagaagtt ttttttttta ctcttgctac tttcctataa agtgatgatt aacaacagat    180
acaccaaaaa gaaaacaatt aatctatatt cacaatgaag cagtactagt ctattgaaca    240
```

```
tgtcagattt tcttttcta  aatgtctaat taagccttca aggctagtga tgataaaaga    300
tcatccaatg ggatccaaca aagactcaaa tctggttttg atcagatact tcaaaactat    360
ttttgtattc attaaattat gcaagtgttc ttttatttgg tgaagactct ttagaagcaa    420
agaacgacaa gcagtaataa aaaaaacaaa gttcagtttt aagatttgtt attgacttat    480
tgtcatttga aaatatagt  atgatattaa tatagtttta tttatataat gcttgtctat    540
tcaagatttg agaacattaa tatgatactg tccacatatc caatatatta agtttcattt    600
ctgttcaaac atatgataga tggtcaaatg attatgagtt tgttatttta cctgaagaaa    660
gataagtgag cttcgagttt ctgaagggta cgtgatcttc atttcttggc taaaagcgaa    720
tatgacatca cctagagaaa gccgataata gtaaactctg ttcttggttt ttggtttaat    780
caaaccgaac cggtagctga gtgtcaagtc agcaaacatc gcaaaccata tgtcaattcg    840
ttagattccc ggtttaagtt gtaaaccggt atttcatttg gtgaaaaccc tagaagccag    900
ccaccctttt taatctaatt tttgtaaacg agaagtcacc acacctctcc actaaaaccc    960
tgaaccttac tgagagaagc agagcgcagc tcaaagaaca aataaaaccc gaagatgaga   1020
ccaccacgtg gcggcgggag cttcagggga cggggaggaa gagatggcgg cggacgcttt   1080
ggtggcggcg gcggacgttt tggtggcggc ggtggacgct ttggtggcgg cggtggacgc   1140
tttggtggtg gtggatatcg tgacgaaggg cctcccagcg aagtcattgg ttcgtttact   1200
ctttacttag tcgaatctta ttcttgctct gctcgttgtt ttaccgataa agctt        1255
```

<210> SEQ ID NO 20
<211> LENGTH: 240
<212> TYPE: DNA
<213> ORGANISM: Umbellularia californica

<400> SEQUENCE: 20

```
atggccacca cctctttagc ttccgctttc tgctcgatga aagctgtaat gttggctcgt     60
gatggccggg gcatgaaacc caggagcagt gatttgcagc tgagggcggg aaatgcgcca    120
acctctttga agatgatcaa tgggaccaag ttcagttaca cggagagctt gaaaaggttg    180
cctgactgga gcatgctctt tgcagtgatc acaaccatct tttcggctgc tgagaagcag    240
```

<210> SEQ ID NO 21
<211> LENGTH: 30
<212> TYPE: DNA
<213> ORGANISM: Artificial Sequence
<220> FEATURE:
<223> OTHER INFORMATION: oligonucleotide primer No.1 for Arabidopsis
      thaliana

<400> SEQUENCE: 21

```
gatatcacta caatgtcgga gagacaaggc                                       30
```

<210> SEQ ID NO 22
<211> LENGTH: 30
<212> TYPE: DNA
<213> ORGANISM: Artificial Sequence
<220> FEATURE:
<223> OTHER INFORMATION: oligonucleotide primer No.2 for Arabidopsis
      thaliana

<400> SEQUENCE: 22

```
ttgtgtatgt tctgtagtga tgagttttgg                                       30
```

<210> SEQ ID NO 23

-continued

<210> SEQ ID NO 23
<211> LENGTH: 28
<212> TYPE: DNA
<213> ORGANISM: Artificial Sequence
<220> FEATURE:
<223> OTHER INFORMATION: oligonucleotide primer No.3 for Arabidopsis
      thaliana

<400> SEQUENCE: 23
agtgtgtata ccacggtgat atgagtgt                                          28

<210> SEQ ID NO 24
<211> LENGTH: 29
<212> TYPE: DNA
<213> ORGANISM: Artificial Sequence
<220> FEATURE:
<223> OTHER INFORMATION: oligonucleotide primer No.4 for Arabidopsis
      thaliana

<400> SEQUENCE: 24
aagctttatc ggtaaaacaa cgagcagag                                         29

<210> SEQ ID NO 25
<211> LENGTH: 47
<212> TYPE: DNA
<213> ORGANISM: Artificial Sequence
<220> FEATURE:
<223> OTHER INFORMATION: oligonucleotide primer No.5 for Arabidopsis
      thaliana

<400> SEQUENCE: 25 ggggggtcgac gatatcacta caatgtcgga gagacaaggc tgcgcca                    47

<210> SEQ ID NO 26
<211> LENGTH: 57
<212> TYPE: DNA
<213> ORGANISM: Artificial Sequence
<220> FEATURE:
<223> OTHER INFORMATION: oligonucleotide primer No.6 for Arabidopsis
      thaliana

<400> SEQUENCE: 26
gctaaagagg tggtggccat ttgtgtatgt tctgtagtga tgagttttgg tttgagt          57

<210> SEQ ID NO 27
<211> LENGTH: 45
<212> TYPE: DNA
<213> ORGANISM: Artificial Sequence
<220> FEATURE:
<223> OTHER INFORMATION: oligonucleotide primer No.7 for Arabidopsis
      thaliana

<400> SEQUENCE: 27 cccccccggga agctttatcg gtaaaacaac gagcagagca agaat                      45

<210> SEQ ID NO 28
<211> LENGTH: 47
<212> TYPE: DNA
<213> ORGANISM: Artificial Sequence
<220> FEATURE:
<223> OTHER INFORMATION: oligonucleotide primer No.8 for Arabidopsis
      thaliana

<400> SEQUENCE: 28 ggggggtcgac gatatcacta caatgtcgga gagacaaggc tgcgcca                    47

<210> SEQ ID NO 29
<211> LENGTH: 50

<212> TYPE: DNA
<213> ORGANISM: Artificial Sequence
<220> FEATURE:
<223> OTHER INFORMATION: oligonucleotide primer No.9 for Arabidopsis
      thaliana

<400> SEQUENCE: 29
catatgccgc ggccgcccac tagtttgtgt atgttctgta gtgatgagtt          50

<210> SEQ ID NO 30
<211> LENGTH: 49
<212> TYPE: DNA
<213> ORGANISM: Artificial Sequence
<220> FEATURE:
<223> OTHER INFORMATION: oligonucleotide primer No.10 for Arabidopsis
      thaliana

<400> SEQUENCE: 30
actagtgggc ggccgcggca tatggtgtgt ataccacggt gatatgagt           49

<210> SEQ ID NO 31
<211> LENGTH: 45
<212> TYPE: DNA
<213> ORGANISM: Artificial Sequence
<220> FEATURE:
<223> OTHER INFORMATION: oligonucleotide primer No.11 for Arabidopsis
      thaliana

<400> SEQUENCE: 31 cccccccggga agctttatcg gtaaaacaac gagcagagca agaat              45

<210> SEQ ID NO 32
<211> LENGTH: 30
<212> TYPE: DNA
<213> ORGANISM: Artificial Sequence
<220> FEATURE:
<223> OTHER INFORMATION: oligonucleotide primer No.12 for Arabidopsis
      thaliana

<400> SEQUENCE: 32
gcggccgcat ggccaccacc tctttagctt                                30

<210> SEQ ID NO 33
<211> LENGTH: 39
<212> TYPE: DNA
<213> ORGANISM: Artificial Sequence
<220> FEATURE:
<223> OTHER INFORMATION: oligonucleotide primer No.13 for Arabidopsis
      thaliana

<400> SEQUENCE: 33
gcggccgctc tagattggtc cactgcttct cagcagccg                      39

<210> SEQ ID NO 34
<211> LENGTH: 37
<212> TYPE: DNA
<213> ORGANISM: Artificial Sequence
<220> FEATURE:
<223> OTHER INFORMATION: oligonucleotide primer No.14 for Arabidopsis
      thaliana

<400> SEQUENCE: 34
tggaccaatc tagagctcga ttccaagaag aggggggg                       37

<210> SEQ ID NO 35
<211> LENGTH: 37
<212> TYPE: DNA

```
<213> ORGANISM: Artificial Sequence
<220> FEATURE:
<223> OTHER INFORMATION: oligonucleotide primer No.15 for Arabidopsis
      thaliana

<400> SEQUENCE: 35
atatgccgcg gccgctcatt tactctcagt tgggtgc                            37

<210> SEQ ID NO 36
<211> LENGTH: 25
<212> TYPE: DNA
<213> ORGANISM: Artificial Sequence
<220> FEATURE:
<223> OTHER INFORMATION: oligonucleotide primer No.16 for Arabidopsis
      thaliana

<400> SEQUENCE: 36
ctctagattg gtccactgct tctca                                         25

<210> SEQ ID NO 37
<211> LENGTH: 23
<212> TYPE: DNA
<213> ORGANISM: Artificial Sequence
<220> FEATURE:
<223> OTHER INFORMATION: oligonucleotide primer No.17 for Arabidopsis
      thaliana

<400> SEQUENCE: 37
gcggccgcgg catatggtgt gta                                           23
```

THIOESTERASE AND A METHOD OF PRODUCING FATTY ACIDS OR LIPIDS USING THE THIOESTERASE

REFERENCE TO SEQUENCE LISTING SUBMITTED ELECTRONICALLY

The content of the electronically submitted substitute sequence listing, file name 2537_0770002_US_SequenceListing_ascii.txt, size 20,142 bytes; and date of creation Nov. 1, 2012, filed herewith, is incorporated herein by reference in its entirety.

TECHNICAL FIELD

The present invention relates to a new thioesterase and a gene that encodes the thioesterase. The present invention also relates to a transformant having a gene that encodes the thioesterase and a method of producing fatty acids or lipids using the thioesterase.

BACKGROUND ART

Fatty acids are one of the principal constituent components of lipids. The fatty acids constitute lipids such as triacylglycerol by bonding to glycerin through an ester bond in vivo, and are stored and utilized as energy sources in many animals and plants. The fatty acids and lipids stored in animals and plants are widely utilized for food or industrial use, for example, intermediate materials of foods, such as monoacylglycerol and diacylglycerol, and additives or intermediate materials for various industrial products. Further, higher alcohol derivatives that are obtained by reducing higher fatty acids having approximately 12 to 18 carbon atoms are used as surfactants. For example, alkyl sulfuric acid ester salts and alkylbenzenesulfonic acid salts are utilized as anionic surfactants, and polyoxyalkylene alkyl ethers and alkyl polyglycosides are utilized as nonionic surfactants, and these surfactants are used for detergents or disinfectants. Likewise, as other higher alcohol derivatives, alkylamine salts and mono- or dialkyl quaternary amine salts are commonly used for fiber treatment agents, hair conditioning agents or disinfectants as cationic surfactants, and benzalkonium type quaternary ammonium salts are commonly used for disinfectants or antiseptics. Particularly, anionic surfactants and nonionic surfactants, each containing an alkyl moiety having approximately 12 carbon atoms, are useful as base materials for washing which exhibit high cleaning power, and cationic surfactants each containing an alkyl moiety having approximately 14 carbon atoms are especially useful as hair rinsing agents or the like. Furthermore, higher alcohols having approximately 18 carbon atoms are also useful as growth promoting agents for plants.

As above, fatty acids are widely used for various applications, and therefore, it has been attempted to enhance the productivity of fatty acids or lipids in vivo by using animals and plants. For example, methods of increasing the lipid content in seeds by introducing acetyl-CoA carboxylase (ACCase) (Patent Literature 1, Non-Patent Literature 1, and Patent Literature 5); methods of increasing the lipid content in seeds by introducing a yeast sn-2 acyltransferase (SLC1-1) (Patent Literature 2, Patent Literature 3 and Non-Patent Literature 2); and methods of increasing the lipid content in seeds by introducing diacylglycerol acyltransferase gene (DGAT) (Patent Literature 4 and Non-Patent Literature 3), have been proposed. Furthermore, it has been attempted to control the number of carbon atoms in a fatty acid (that is, the fatty acid chain length), since the utility or usefulness of fatty acids depends largely on the number of carbon atoms. For example, methods of accumulating fatty acids having 12 carbon atoms by introducing a *Umbellularia californica* (California bay)-derived Acyl-ACP thioesterase (Patent Literature 6 and Non-Patent Literature 4); a method of accumulating fatty acids having 8 or 10 carbon atoms by introducing a *Cuphea hookeriana*-derived Acyl-ACP thioesterase (Patent Literature 7); and a method of accumulating fatty acids having 14 carbon atoms by introducing a *Cinnamomum camphorum*-derived Acyl-ACP thioesterase (Non-Patent Literature 5), have been proposed.

CITATION LIST

Patent Literatures

Patent Literature 1: JP-A-2002-335786 ("JP-A" means unexamined published Japanese patent application)
Patent Literature 2: JP-A-11-506323
Patent Literature 3: WO 2008/076377 pamphlet
Patent Literature 4: WO 2000/036114 pamphlet
Patent Literature 5: U.S. Pat. No. 5,925,805
Patent Literature 6: JP-A-7-501924
Patent Literature 7: JP-A-8-502892

Non-Patent Literatures

Non-Patent Literature 1: Madoka Y, Tomizawa K, Mizoi J, Nishida I, Nagano Y, Sasaki Y., "Chloroplast transformation with modified accD operon increases acetyl-CoA carboxylase and causes extension of leaf longevity and increase in seed yield in tobacco", Plant Cell Physiol., 2002 December, 43 (12), p. 1518-1525
Non-Patent Literature 2: Zou J. Katavic V, Giblin E M, Barton D L, MacKenzie S L, Keller W A, Hu X, Taylor D C., "Modification of seed oil content and acyl composition in the brassicaceae by expression of a yeast sn-2 acyltransferase gene", Plant Cell, 1997 June, 9 (6), p. 909-923
Non-Patent Literature 3: Jako C. Kumar A, Wei Y. Zou J. Barton D L, Giblin E M, Covello P S, Taylor D C., "Seed-specific over-expression of an *Arabidopsis* cDNA encoding a diacylglycerol acyltransferase enhances seed oil content and seed weight", Plant Physiol., 2001, 126 (2), p. 861-874
Non-Patent Literature 4: Voelker T A, Worrell A C, Anderson L. Bleibaum J. Fan C. Hawkins D J, Radke S E, Davies H M., "Fatty acid biosynthesis redirected to medium chains in transgenic oilseed plants", Science, 1992 Jul. 3; 257 (5066), p. 72-74.
Non-Patent Literature 5: Yuan L. Voelker T A, Hawkins D J. "Modification of the substrate specificity of an acyl-acyl carrier protein thioesterase by protein engineering", Proc. Natl. Acad. Sci. U.S.A., 1995 Nov. 7; 92 (23), p. 10639-10643.

SUMMARY OF INVENTION

Problems that the Invention is to Solve

The present invention is contemplated for providing a new thioesterase and a thioesterase gene that encodes the thioesterase. The present invention is also contemplated for providing a transformant introduced with the thioesterase gene and has an enhanced ability to produce fatty acids or lipids containing fatty acids. Further, the present invention is contemplated for providing a method of producing fatty acids or lipids containing fatty acids using the transformant.

Means to Solve the Problem

The present inventors made extensive studies so as to enhance the lipid productivity in animals and plants. The inventors paid attention to the enzyme, thioesterase, which takes a key role in the biosynthesis of fatty acids and lipids in living organisms, and attempted a search for a new thioesterase which can be produced with higher productivity than conventional enzymes. The inventors isolated a gene that encodes a novel thioesterase from *Cocos nucifera* L. (coconut palm), and then introduced the gene into a host to obtain a transformant. As a result, the inventors found that, in the transformant, the productivity of fatty acids or lipids significantly increases as compared with transformants having other thioesterase genes introduced therein, and the composition of fatty acids contained in the lipids is different from the composition of the *Cocos nucifera* L. endosperm. The present invention was completed based on these findings.

The present invention relates to a protein selected from the following (a) to (c) (hereinafter, referred to as "the protein(s) of the present invention"):
(a) A protein comprising an amino acid sequence set forth in SEQ ID NO: 1, and having thioesterase activity,
(b) A protein comprising an amino acid sequence in which one to several amino acids are deleted, substituted, inserted and/or added in the amino acid sequence set forth in SEQ ID NO: 1, and having thioesterase activity, and
(c) A protein comprising an amino acid sequence having at least 90% sequence identity (homology) to the amino acid sequence set forth in SEQ ID NO: 1, and having thioesterase activity.

The present invention also relates to a gene encoding the protein of the present invention (hereinafter, referred to as "the gene(s) of the present invention"), preferably a gene comprising any one of DNAs of the following (d) to (f):
(d) A DNA comprising a nucleotide sequence set forth in SEQ ID NO: 2, which codes a protein having thioesterase activity,
(e) A DNA capable of hybridizing with a DNA comprising a complementary sequence to the nucleotide sequence set forth in SEQ ID NO: 2 under a stringent condition, which codes a protein having thioesterase activity, and
(f) A DNA comprising a nucleotide sequence having at least 90% sequence identity (homology) to the nucleotide sequence set forth in SEC) ID NO: 2, which codes a protein having thioesterase activity.

The present invention also relates to a recombinant vector comprising the gene, and a transformant comprising the gene or the recombinant vector.

The present invention also relates to a method of producing a fatty acid or a lipid containing a fatty acid, comprising culturing the transformant in a culture medium, and collecting a fatty acid (preferably lauric acid, myristic acid, palmitic acid and palmitoleic acid) or a lipid containing a fatty acid, from the culture of the medium.

The present invention also relates to a method of enhancing productivity of a fatty acid or a lipid containing a fatty acid, comprising introducing the gene that encodes any one of the proteins of the above (a) to (c), into a host.

Effects of the Invention

The present invention provides a new thioesterase and a gene that encodes the thioesterase. The present invention also provides a transformant introduced with the thioesterase gene and having an enhanced ability to produce fatty acids or lipids. Further, the present invention provides a method of producing fatty acids (preferably lauric acid, myristic acid, palmitic acid, and palmitoleic acid) or lipids using the transformant. The transformant and the production method of the present invention provide fatty acids and lipids having a characteristic fatty-acid-composition with excellent productivity, and therefore they can be suitably used for the industrial production of fatty acids and lipids.

Other and further features and advantages of the invention will appear more fully from the following description, taken in connection with the accompanying drawings.

BRIEF DESCRIPTION OF DRAWINGS

FIG. 1 is a diagram showing the contents of the individual fatty acids in transformed *Escherichia coli* cells introduced with the thioesterase (BTE) gene derived from *Umbellularia californica* or the thioesterase (CTE) gene derived from *Cocos nucifera* L.

FIG. 2 is a diagram showing the total content of the individual fatty acids in transformed *Escherichia coli* cells introduced with the thioesterase (BTE) gene derived from *Umbellularia californica* or the thioesterase (CTE) gene derived from *Cocos nucifera* L.

FIG. 3(a) is a diagram showing the composition ratios of fatty acids in the *Cocos nucifera* L. endosperm, and FIG. 3(b) is a diagram showing the composition ratios of fatty acids in a transformant introduced with the thioesterase (CTE) gene derived from *Cocos nucifera* L.

FIG. 4 is a diagram showing the total contents of the individual fatty acids contained in seeds obtained from a wild strain of *Arabidopsis thaliana*, and an *Arabidopsis thaliana* transformant: Pnapin-CTE introduced with the thioesterase gene derived from *Cocos nucifera* L.

FIG. 5 is a diagram showing the composition ratios of fatty acids in seeds of a wild-type strain of *Arabidopsis thaliana* and an *Arabidopsis thaliana* transformant: Pnapin-CTE introduced with the thioesterase gene derived from *Cocos nucifera* L.

MODE FOR CARRYING OUT THE INVENTION

1. Enzyme Thioesterase

Figure 1:
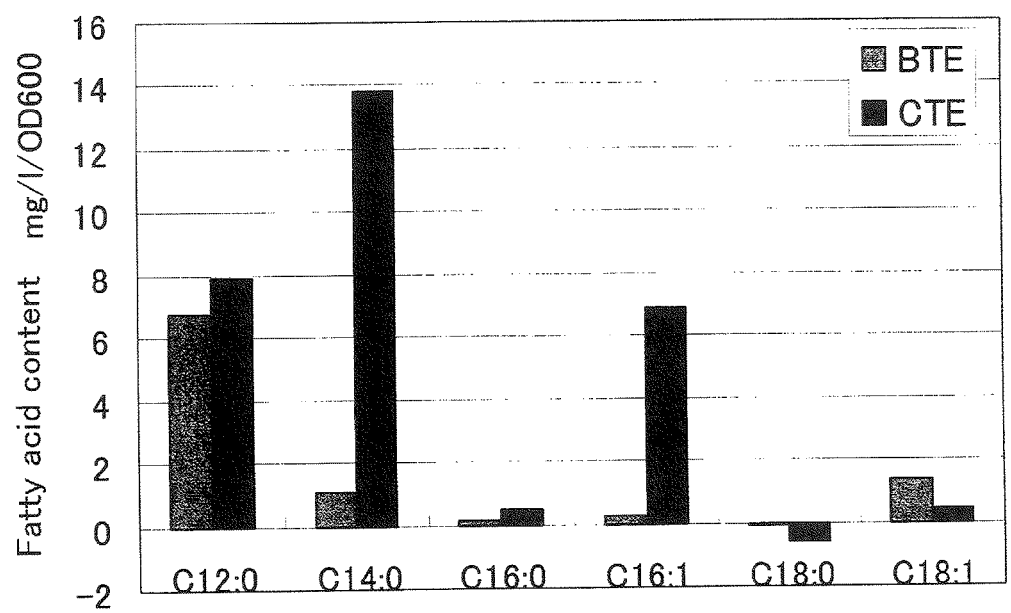
{FIG. 1}

The protein of the present invention is any one of proteins of the following (a) to (c) (hereinafter, referred to as "thioesterase of the present invention"):
(a) A protein comprising an amino acid sequence set forth in SEQ ID NO: 1, and having thioesterase activity,
(b) A protein comprising an amino acid sequence in which one to several amino acids are deleted, substituted, inserted and/or added in the amino acid sequence set forth in SEQ ID NO: 1, and having thioesterase activity, and
(c) A protein comprising an amino acid sequence having at least 90% sequence identity (homology) to the amino acid sequence set forth in SEQ ID NO: 1, and having thioesterase activity.

The gene of the present invention is a gene encoding the protein.

The protein having the amino acid sequence set forth in SEQ ID NO: 1 is a novel thioesterase derived from *Cocos nucifera* L. (hereinafter, the novel thioesterase is also referred to as "CTE")

Thioesterases are acyl-acyl carrier protein (Acyl-ACP) thioesterases which are enzymes involved in the triglyceride biosynthesis pathway. Thioesterases hydrolyze a thioester bond of an acyl-acyl carrier protein to form free fatty acids. The acyl-acyl carrier protein is a composite composed of an acyl group as a fatty acid residue and an acyl carrier protein, and is an intermediate in the process of fatty acid biosynthesis in chloroplasts or plastids. Thioesterases catalyze the fatty acid synthesis on the acyl carrier protein to generate free fatty acids, and then the free fatty acids are transported from the plastids and supplied to the triglyceride synthesis. Thioesterases have different reaction specificities depending on the type of the fatty acid residue constituting the acyl-acyl carrier protein, and therefore, the thioesterases are an important factor in determining fatty acid composition of an organism.

The protein of the present invention includes (a) a protein comprising the amino acid sequence set forth in SEQ ID NO: 1 and having thioesterase activity, as well as proteins that are functionally equivalent to the protein (a).

In amino acid sequences encoding enzyme proteins, it is generally known that to conserve the complete amino acid sequence of an enzyme is not always necessary for its activity, and that a change of the original sequence has little or no effect on the enzyme activity in some regions. In such a region that is not essential to the enzyme activity, the enzyme activity can be maintained even if some variations (mutations) such as deletions, substitutions, insertions or additions are introduced into the amino acid of the region. Likewise, the present invention can be used the variants in which the amino acid sequences set forth in SEQ ID NO: 1 are partially changed while keeping the thioesterase activity.

The proteins that are functionally equivalent to the thioesterase comprising the amino acid sequence set forth in SEQ ID NO: 1 include the following proteins (b) and (c). These proteins (b) and (c) are encompassed by the proteins of the present invention.

(b) A protein comprising an amino acid sequence in which one to several amino acids are deleted, substituted, inserted and/or added in the amino acid sequence set forth in SEQ ID NO: 1, and having thioesterase activity.

(c) A protein comprising an amino acid sequence having at least 90% sequence identity (homology) to the amino acid sequence set forth in SEQ ID NO: 1, and having thioesterase activity.

In the protein (b), the number of amino acids that are deleted, substituted, inserted and/or added is preferably 1 to 20, more preferably 1 to 10, still more preferably 1 to 5, and particularly preferably 1 to 2. The added as described above includes addition of one to several amino acids to both ends.

In the protein (c), the sequence identity (homology) of amino acid sequence is preferably 95% or more, more preferably 96% or more, still more preferably 97% or more, and particularly preferably 98% or more.

The inventors compared the amino acid sequence of the thioesterase set forth in SEQ ID NO: 1 with amino acid sequences of other known thioesterases, as shown in the Examples described below. As a result, the sequence identities between the thioesterase of the present invention and other known thioesterases were about 50% to 60%. For example, the identity with the amino acid sequence of a California bay (*Umbellularia californica*; also called California bay tree)-derived thioesterase was about 50%, and the identity with the amino acid sequence of an *Arabidopsis thaliana*-derived thioesterase is about 60%.

The sequence identity (homology) of the amino acid sequence and nucleotide sequence is calculated through the Lipman-Pearson method (see Science, 227, pp. 1435, (1985)). Specifically, the identity can be determined through use of a homology analysis (Search homology) program of genetic information processing software Genetyx-Win (Software Development Co., Ltd.) with the unit size to compare (ktup) being set to 2.

Among the proteins of (b) and (c) described above, it is preferable a thioesterase variant having thioesterase activity and having an amino acid sequence in which the amino acids corresponding to the specific residues in the amino acid sequence set froth in SEQ ID NO: 1 are conserved as follows: the $34^{th}$ residue is arginine; the $35^{th}$ residue is serine; the $37^{th}$ residue is glutamic acid; the $39^{th}$ residue is glycine; the $41^{st}$ residue is aspartic acid; the $51^{st}$ residue is asparagine; the $54^{th}$ residue is glutamine; the $59^{th}$ residue is asparagine; the $65^{th}$ residue is glycine; the $70^{th}$ residue is glycine; the $72^{nd}$ residue is glycine; the $74^{th}$ residue is threonine; the $77^{th}$ residue is methionine; the $82^{nd}$ residue is leucine; the $84^{th}$ residue is tryptophan; the $85^{th}$ residue is valine; the $96^{th}$ residue is tyrosine; the $98^{th}$ residue is tryptophan; the $99^{th}$ residue is tryptophan; the $108^{th}$ residue is tryptophan; the $113^{th}$ residue is glycine; the $137^{th}$ residue is serine; the $142^{nd}$ residue is methionine; the $147^{th}$ residue is arginine; the $177^{th}$ residue is lysine; the $192^{nd}$ residue is glycine; the $193^{rd}$ residue is leucine; the $195^{th}$ residue is proline; the $197^{th}$ residue is tryptophan; the $199^{th}$ residue is aspartic acid; the $201^{st}$ residue is aspartic acid; the $203^{rd}$ residue is asparagine; the $205^{th}$ residue is histidine; the $206^{th}$ residue is valine; the $210^{th}$ residue is lysine; the $211^{th}$ residue is tyrosine; the $214^{th}$ residue is tryptophan; the $220^{th}$ residue is proline; the $236^{th}$ residue is tyrosine; the $239^{th}$ residue is glutamic acid; the $248^{th}$ residue is serine; the $266^{th}$ residue is histidine; and the $283^{rd}$ residue is tryptophan, and in which the amino acids other than the above residues are partially altered.

The thioesterase of the present invention has the following features.

(1) A transformant having the thioesterase of the present invention introduced therein has superior productivity for fatty acids or lipids as compared with transformants having other plant thioesterases (for example, a *Umbellularia californica*-derived thioesterase) introduced therein.

(2) A transformant having the thioesterase of the present invention introduced therein produce fatty acids having a different composition from that of the *Cocos nucifera* L. endosperm. Specifically, the production of myristic acid (C14:0) is increased. Furthermore, unsaturated fatty acids that are hardly observed in the *Cocos nucifera* L. endosperm (particularly, palmitoleic acid of C16:1) are produced.

(3) In a transformant having the thioesterase of the present invention introduced therein, lauric acid (C12:0), myristic acid (C14:0), palmitic acid (C16:0), and palmitoleic acid (C16:1) are primarily produced.

In the present invention, the "having thioesterase activity" means having an activity of hydrolyzing a thioester bond of an acyl-acyl carrier protein. The thioesterase activity of a protein can be measured by, for example, introducing a fusion gene produced by linking the thioesterase gene to the downstream of a promoter which functions in host cells such as *Escherichia coli*, into a host cell which lacks a fatty acid degradation system, culturing the host cell under the conditions suitable for the expression of the introduced thioesterase gene, and analyzing any change caused thereby in the fatty acid composition of the host cell by using a gas chromatographic analysis or the like. Alternatively, the thioesterase activity can be measured by introducing a fusion gene produced by linking the thioesterase gene to the downstream of a promoter which functions in the host cells such as *Escherichia coli*, into a host cell, culturing the host cell under the conditions suitable for the expression of the introduced thioesterase gene, and subjecting a disruption liquid of the cell to a reaction which uses Acyl-ACPs, as substrates, prepared according to the method of Yuan et al., PNAS, 1995, (92), p. 10639-10643 (Non-Patent Literature 5 as described above).

There are no particular limitations on the method for obtaining the protein of the present invention, and the protein may be obtained by chemical techniques or genetic engineering techniques that are conventionally carried out. For example, a natural product-derived protein can be obtained through isolation, purification and the like from the *Cocos nucifera* L. endosperm. Furthermore, the protein can also be artificially synthesized based on the information for the amino acid sequence set forth in SEQ ID NO: 1, and protein synthesis may be carried out by chemical synthesis, or a recombinant protein may also be produced by gene recombination technologies. In the case of producing a recombinant protein, the thioesterase gene of the present invention that will be described below can be used.

2. Thioesterase Gene

The gene of the present invention is a gene encoding the protein of the present invention described above (hereinafter, referred to as "thioesterase gene of the present invention"). The gene of the present invention preferably includes (d) a gene comprising a DNA comprising the nucleotide sequence set forth in SEQ ID NO: 2 and coding a protein having thioesterase activity, as well as genes that are functionally equivalent to the gene (d).

The genes that are functionally equivalent to the thioesterase gene comprising a DNA comprising the nucleotide sequence set forth in SEQ ID NO: 2 include the following genes (e) to (g). These genes (e) to (g) are encompassed by the genes of the present invention.

(e) A gene comprising a DNA capable of hybridizing with a DNA comprising a complementary sequence to the nucleotide sequence set forth in SEQ ID NO: 2 under a stringent condition, which codes a protein having thioesterase activity (f) A gene comprising a DNA comprising a nucleotide sequence having at least 90% sequence identity (homology) to the nucleotide sequence set forth in SEQ ID NO: 2, which codes a protein having thioesterase activity (g) A gene comprising a DNA comprising a nucleotide sequence in which one to several nucleotides are deleted, substituted, inserted and/or added in the nucleotide sequence set forth in SEQ ID NO: 2, which codes a protein having thioesterase activity The "stringent condition" above is, for example, the condition described in "Molecular Cloning—A LABORATORY MANUAL THIRD EDITION" [Joseph Sambrook, David W. Russell, Cold Spring Harbor Laboratory Press]. It is, for example, a hybridization condition of a gene with a probe by incubation thereof in a solution containing 6×SSC (1×SSC composition: 0.15 M sodium chloride and 0.015 M sodium citrate, pH 7.0), 0.5% SDS, 5×Denhardt and 100 mg/mL herring sperm DNA at 65° C. for 8 to 16 hours.

In the gene (f), the sequence identity (homology) of nucleotide sequence is preferably 95% or more, more preferably 96% or more, still more preferably 97% or more, and particularly preferably 98% or more.

The sequence identity (homology) of the nucleotide sequence is calculated through the Lipman-Pearson method (see Science, 227, pp. 1435 (1985)) described above. Specifically, the identity can be determined through use of a homology analysis (Search homology) program of genetic information processing software Genetyx-Win (Software Development Co., Ltd.) with the unit size to compare (ktup) being set to 2.

In the gene (g), the number of nucleotides that are deleted, substituted, inserted and/or added is preferably 1 to 60, more preferably 1 to 30, still more preferably 1 to 15, and particularly preferably 1 to 6. The added as described above includes addition of one to several amino acids to both ends.

Among the genes of (e) to (g) described above, it is preferable a gene comprising a nucleotide sequence which corresponds to an amino acid sequence in which the amino acids corresponding to the following specific residues in the amino acid sequence set froth in SEQ ID NO: 1 are conserved: the 34$^{th}$ residue is arginine; the 35$^{th}$ residue is serine; the 37$^{th}$ residue is glutamic acid; the 39$^{th}$ residue is glycine; the 41$^{st}$ residue is aspartic acid; the 51$^{st}$ residue is asparagine; the 54$^{th}$ residue is glutamine; the 59$^{th}$ residue is asparagine; the 65$^{th}$ residue is glycine; the 70$^{th}$ residue is glycine; the 72$^{nd}$ residue is glycine; the 74$^{th}$ residue is threonine; the 77$^{th}$ residue is methionine; the 82$^{nd}$ residue is leucine; the 84$^{th}$ residue is tryptophan; the 85$^{th}$ residue is valine; the 96$^{th}$ residue is tyrosine; the 98$^{th}$ residue is tryptophan; the 99$^{th}$ residue is tryptophan; the 108$^{th}$ residue is tryptophan; the 113$^{th}$ residue is glycine; the 137$^{th}$ residue is serine; the 142$^{nd}$ residue is ethionine; the 147$^{th}$ residue is arginine; the 177$^{th}$ residue is lysine; the 192$^{nd}$ residue is glycine; the 193$^{rd}$ residue is leucine; the 195$^{th}$ residue is proline; the 197$^{th}$ residue is tryptophan; the 199$^{th}$ residue is aspartic acid; the 201$^{st}$ residue is aspartic acid; the 203$^{rd}$ residue is asparagine; the 205$^{th}$ residue is histidine; the 206$^{th}$ residue is valine; the 210$^{th}$ residue is lysine; the 211$^{th}$ residue is tyrosine; the 214$^{th}$ residue is tryptophan; the 220$^{th}$ residue is proline; the 236$^{th}$ residue is tyrosine; the 239$^{th}$ residue is glutamic acid; the 248$^{th}$ residue is serine; the 266$^{th}$ residue is histidine; and the 283$^{rd}$ residue is tryptophan, and, in the nucleotide sequence, nucleotides which correspond to the amino acids other than the above conserved amino acid residues are partially altered, and the nucleotide sequence codes a protein having thioesterase activity.

The method of obtaining the thioesterase gene of the present invention is not particularly limited, and the thioesterase gene can be obtained by conventional genetic engineering techniques. For example, the thioesterase gene of the present invention can be obtained by artificial synthesis based on the amino acid sequence set forth in SEQ ID NO: 1 or the nucleotide sequence set forth in SEQ ID NO: 2. The artificial synthesis of a gene can be achieved by utilizing the services such as Invitrogen, Inc. Furthermore, the gene can also be obtained by cloning from *Cocos nucifera* L., and the cloning can be carried out by, for example, the methods described in Molecular Cloning—A LABORATORY MANUAL THIRD EDITION [Joseph Sambrook, David W. Russell, Cold Spring Harbor Laboratory Press (2001)] and the like.

When mutations are introduced into the amino acid sequence set forth in SEQ ID NO: 1 or the nucleotide sequence set forth in SEQ ID NO: 2, it can be used a method for introducing site-specific mutation and the like. Examples of the method for introducing site-specific mutation include a method of utilizing the splicing overlap extension (SOE) PCR (Horton et al., Gene 77, 61-68, 1989); the ODA method (Hashimoto-Gotoh et al., Gene, 152, 271-276, 1995); and the Kunkel method (Kunkel, T. A., Proc. Natl. Acad. Sci. USA, 1985, 82, 488). Furthermore, commercially available kits such as the Site-Directed Mutagenesis System Mutan-Super-Express Km kit (Takara Bio, Inc.), the Transformer TM Site-Directed Mutagenesis kit (Clonetech Laboratories, Inc.), and the KOD-Plus-Mutagenesis kit (Toyobo Co., Ltd.) can also be utilized. Furthermore, the gene containing mutations can also be obtained by introducing genetic mutations at random, and then performing an evaluation of the enzyme activities and a gene analysis thereof by appropriate methods. Specifically, random gene mutations can be introduced by homologous recombination with a DNA fragment that has been randomly cloned, or by irradiating γ-radiation or the like.

3. Transformant

The transformant of the present invention includes the thioesterase gene of the present invention or a recombinant vector which contains the thioesterase gene. As will be discussed in the Examples that will be described below, the transformant of the present invention has the production capacity for fatty acids, preferably long-chain fatty acids having 12 or more carbon atoms, and more preferably lauric acid, myristic acid, palmitic acid and palmitoleic acid, or lipids containing those fatty acids, enhanced to a large extent. In the present invention, the ability to produce fatty acids of the transformant can be measured by the method used in the Examples described below.

The transformant of the present invention is obtained by introducing the thioesterase gene into a host according to a conventional genetic engineering method. Preferably, the transformant can be produced by preparing a recombinant vector which is capable of expressing the thioesterase gene in a host cell, introducing this vector into host cells, and thereby transforming the host cells. The transformant obtained exhibits an enhanced ability to produce fatty acids or lipids containing fatty acids.

First, a recombinant vector comprising the thioesterase gene of the present invention will be described.

The vector used may be any vector capable of introducing the thioesterase gene of the present invention into a host, and expressing the gene in the host cells. For example, an expression vector which has expression regulation regions such as a promoter and a terminator in accordance with the type of the host to be used, and has a replication initiation point, a selection marker or the like, can be used. Furthermore, the vector may also be a vector which is capable of self-proliferation and self-replication outside the chromosome, such as a plasmid, or may also be a vector which is incorporated into the chromosome.

Specific examples of the vector include, in the case of using a microorganism as the host, pBluescript II SK(−) (manufactured by Stratagene Corp.), pUC119 (manufactured by Takara Shuzo Co., Ltd.), a pET-based vector (manufactured by Takara Bio, Inc.), a pGEX-based vector (manufactured by GE Healthcare, Inc.), a pCold-based vector (manufactured by Takara Bio, Inc.), pHY300PLK (manufactured by Takara Bio, Inc.), pUB110 (Mckenzie, T. et al., (1986). Plasmid 15(2); p. 93-103), pBR322 (manufactured by Takara Bio, Inc.), pRS403 (manufactured by Stratagene Corp.), and pMW218/219 (manufactured by Nippon Gene Co., Ltd.). In the case of using a plant cell as the host, examples of the vector include a pRI-based vector (manufactured by Takara Bio, Inc.), a pBI-based vector (manufactured by Clontech Laboratories, Inc.), and an IN3-based vector (manufactured by Inplanta Innovations, Inc.). Particularly, in the case of using *Escherichia coli* as the host, pBluescript II SK(−) (manufactured by Stratagene Corp.) and pMW218/219 (manufactured by Nippon Gene Co., Ltd.) are used preferably. In the case of using *Arabidopsis thaliana* as the host, a pRI-based vector (manufactured by Takara Bio, Inc.) and a pBI-based vector (manufactured by Clontech Laboratories, Inc.) are used preferably.

The expression regulation regions such as a promoter and a terminator, and the selection marker are not particularly limited, and can be appropriately selected from conventionally used promoters, markers and the like in accordance with the type of the host to be used. Specific examples of the promoter include lac promoter, trp promoter, tac promoter, trc promoter, T7 promoter, SpoVG promoter, cauliflower mosaic virus 35S RNA promoter, promoters for housekeeping genes such as actin and ubiquitin, rapeseed-derived *Napin* gene promoter, and plant-derived Rubisco promoter. Examples of the selection marker include drug resistance genes such as antibiotic resistance genes (ampicillin resistance gene, chloramphenicol resistance gene, erythromycin resistance gene, neomycin resistance gene, kanamycin resistance gene, spectinomycin resistance gene, tetracycline resistance gene, blasticidin S resistance gene, bialaphos resistance gene, and hygromycin resistance gene). Further, it is also possible to use a deletion of an auxotrophy-related gene or the like as a selection marker.

A vector for transformation can be constructed by introducing the thioesterase gene of the present invention into the above-described vector according to a conventional technique such as restriction enzyme treatment or ligation. The thioesterase gene of the present invention can be obtained by the method described above.

The recombinant vector can introduce the thioesterase gene into a host to construct a transformant.

The host for the transformant is not particularly limited, and a microorganism, a plant or an animal can be used. The thioesterase of the present invention can be used for producing long-chain fatty acids, particularly fatty acids having 12 or more carbon atoms described below. Even an organism which inherently does not have a thioesterase that recognizes a fatty acid residue having 12 carbon atoms as a substrate, can also be used as the host. According to the present invention, it is preferable to use a microorganism and a plant as the host, from the viewpoints of production efficiency of fatty acids and lipids and the usability of fatty acids derived from them. As the microorganism, prokaryotes such as microorganisms which belong to the genus *Escherichia* or microorganisms which belong to the genus *Bacillus*; or eukaryotes such as yeast or filamentous fungi can be used. Among them, *Escherichia coli, Bacillus subtilis, Rhodosporidium toruloides*, and *Mortierella* sp. are preferred, and *Escherichia coli* is particularly preferred. As the plant, *Arabidopsis thaliana*, rapeseed, coconut, palm, *cuphea*, and Jatropha are preferred, and *Arabidopsis thaliana* is particularly preferred.

The method for transformation is not particularly limited as long as it is a method capable of introducing a target gene into a host. For example, a method of using calcium ion, a general competent cell transformation method (J. Bacterial. 93, 1925 (1967)), a protoplast transformation method (Mol. Gen. Genet. 168, 111 (1979)), an electroporation method (FEMS Microbiol. Lett. 55, 135 (1990)), an LP transformation method (T. Akamatsu and J. Sekiguchi, Archives of Microbiology, 1987, 146, p. 353-357; T. Akamatsu and H. Taguchi, Bioscience, Biotechnology, and Biochemistry, 2001, 65, 4, p. 823-829) and the like, can be used.

Further, the selection of a transformant having a target gene fragment introduced therein can be carried out by using a selection marker or the like. For example, the selection can be carried out by using an indicator whether a transformant acquires the drug resistance as a result of introducing a vector-derived drug resistance gene into a host cell together with a target DNA fragment. Further, the introduction of a target DNA fragment can also be confirmed by PCR using a genome as a template.

4. Method of Producing Fatty Acid and Lipid

The method of producing fatty acids or lipids containing fatty acids of the present invention uses the thioesterase of the present invention described above. Specifically, a method of using a transformant (recombinant microorganisms, plants or the like) containing the thioesterase gene of the present invention, and a method of performing the excision of a fatty acid from Acyl-ACP in vitro using a purified Acyl-ACP and the thioesterase of the present invention to produce fatty acids or lipids (Yuan et al., PNAS, 1995, (92), p. 10639-10643), can be used. Particularly, it is preferable to a method by preparing a transformant having a gene that encodes the thioesterase of the present invention introduced therein, by the techniques described above, subsequently culturing the transformant under appropriate conditions using an appropriate medium to produce fatty acids or lipids containing these fatty acids, and thereby collecting the fatty acids or lipids from the culture. Meanwhile, the operation of culturing a transformant in a medium according to the present invention includes culturing of a microorganism, an animal, a plant, or cell tissues thereof, as well as cultivating a plant in a soil or the like. Furthermore, the culture also includes the transformant itself that has been cultured or cultivated.

The conditions for culture and growth of a transformant can be selected in accordance with the type of the host having the thioesterase gene introduced therein, and any appropriate preferred conditions can be employed. For instance, in the case of using *Escherichia coli* as the host for transformation, culture may be carried out in LB medium at 30° C. to 37° C. for half a day to 1 day. In the case of a using *Arabidopsis thaliana* as the host for transformation, growth may be carried out in the soil under the temperature conditions of 20° C. to 25° C., by continuously irradiating white light or under the illumination conditions of a light period of 16 hours and a dark period of 8 hours, for one to two months.

From the viewpoint of the production efficiency of fatty acids and lipids, substrates for thioesterase or precursor substances participating in the fatty acid biosynthesis pathway, such as glycerol, acetic acid, malonic acid and the like, may be added to the medium.

After fatty acids or lipids are produced by culturing and growing the transformant, these fatty acids and lipids containing fatty acids are collected from the culture (the transformant, culture medium or the like) by performing isolation, purification and the like.

The method of isolating and collecting fatty acids or lipids containing fatty acids produced in the transformant are not particularly limited, and the conventional method that are used to isolate lipid components and the like from organisms may be used. For example, fatty acids or lipids containing fatty acids can be isolated and collected from the culture or the transformant by means of filtration, centrifugation, cell disruption, gel filtration chromatography, ion exchange chromatography, chloroform/methanol extraction, hexane extraction, ethanol extraction, or the like. In the case of isolation and collection of larger scales, lipids can be obtained by collecting oil components from the culture or the transformant through pressing or extraction, and then performing general purification processes such as degumming, deacidification, decoloration, dewaxing, and deodorization. After lipid components containing fatty acids are isolated as such, fatty acids can be obtained by hydrolyzing the isolated lipids. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

In this way, fatty acids or lipids can be produced by using the thioesterase gene of the present invention.

The production method of the present invention can be preferably used in the production of long-chain fatty acids having 12 or more carbon atoms or lipids containing these fatty acids, more preferably used in the production of fatty acids having 12 to 18 carbon atoms or lipids containing these fatty acids, still more preferably used in the production of fatty acids having 12 to 16 carbon atoms or lipids containing these fatty acids, particularly preferably used in the production of lauric acid (C12:0), myristic acid (C14:0), palmitic acid (C16:0), and palmitoleic acid (C16:1).

The fatty acids or derivatives thereof obtained by the production method and the transformant of the present invention can be utilized for food, as well as can be utilized as an emulsifier incorporated into cosmetic products or the like, a cleansing agent such as a soap or a detergent, a fiber treatment agent, a hair conditioning agent, a disinfectant or an antiseptic. Particularly, palmitoleic acid can be used as a skin function improving agent (a skin softening effect, a skin protective effect, an anti-inflammatory effect, alleviation effects of itchiness and irritation, a soothing effect of a light scald, and the like).

EXAMPLES

Hereinafter, the present invention will be described more in detail with reference to Examples, but the present invention is not limited thereto.

Example 1

Isolation of Acyl-ACP thioesterase gene derived from *Cocos nucifera* L.

1. Preparation of cDNA from *Cocos nucifera* L. Endosperm

RNA was extracted from the *Cocos nucifera* L. endosperm. For the RNA extraction, an RNeasy Plant Mini Kit (Qiagen, Valencia, Calif.) was used. The *Cocos nucifera* L. endosperm was frozen with liquid nitrogen and then was powdered by using a mortar and a pestle. An appropriate amount of the powdered product was transferred to a 1.5-mL tube, 450 μL of an RLT buffer containing a 1/100 volume of 1 M dithiothreitol was added to the tube, and the mixture was vortexed. The entire amount was applied to a QIA shredder spin column. Thereafter, the operation was carried out according to the manual attached to the kit, and *Cocos nucifera* L.-derived total RNA was obtained. The total RNA (3.2 μg) was used as a template for a reverse transcription reaction. The reaction was carried out by using a SuperScript III First-Strand Synthesis System (Invitrogen, Carlsbad, Calif.) according to the manual attached to the kit, and a *Cocos nucifera* L. endosperm-derived cDNA was obtained.

2. Cloning of *Cocos nucifera* L.-Derived Thioesterase Gene (CTE Gene)

The genomic information for *Cocos nucifera* L. and the genetic information on the *Cocos nucifera* L.-derived Acyl-ACP thioesterase are not known. Thus, amino acid sequences highly conserved among various plant thioesterases that are already known were selected, and degenerate primers corresponding those regions were designed as indicated in Table 1 (Primers No. 1 to No. 5 (SEQ ID NOs: 5 to 9)). Specifically, degenerate primers were designed for plant thioesterase sequences corresponding to the amino acids at the $105^{th}$ to $110^{th}$ positions (AAEKQW), the $250^{th}$ to $255^{th}$ positions (VVVMMN), the $310^{th}$ to $318^{th}$ positions (DLDVNQHV), and the $315^{th}$ to $324^{th}$ positions (NQHVNNVKY) in the *Arabidopsis thaliana* thioesterase (Genbank ID (GI): 804947). A PCR reaction was carried out by using the *Cocos nucifera* L.

endosperm-derived cDNA as a template and using the degenerate primers. Various DNA fragments were obtained from the PCR reaction and those sequences were determined by sequence analysis. Particularly, partial sequence information for the CTE gene was obtained by sequence alignment based on the sequences obtained by the PCR reaction using Primers No. 2 and No. 4. Based on the partial sequence information, an oligo-DNA primer (Table 1, Primer No. 6 (SEQ ID NO: 10)) and an oligo-dT primer (Table 1, Primer No. 7 (SEQ ID NO: 11)) were designed, and then a PCR reaction was carried out by using these primers to amplify a DNA fragment. A sequence analysis of the amplified DNA fragment was carried out, and as a result, the nucleotide sequence of a gene encoding the functional part of the *Cocos nucifera* L.-derived thioesterase was obtained and verified (SEQ ID NO: 2).

TABLE 1

Table 1 Primer Sequence

| Primer No. | Sequence* | SEQ ID NO. |
|---|---|---|
| 1 | ttyathaaycarytnccngaytgg | 5 |
| 2 | gcngcngaraarcartgg | 6 |
| 3 | rtayttnacrttrttnacrtgytgrtt | 7 |
| 4 | rttcatcatnaccca | 8 |
| 5 | acrtgytgrttnacrtcnarrtc | 9 |
| 6 | cagtggaccctgctcgattc | 10 |
| 7 | tttttttttttttttttttttttt | 11 |
| 8 | caggtcgactctagagctcgattccaagaagaggggggc | 12 |
| 9 | ggtacccggggatcctcatttactctcagttgg | 13 |
| 10 | ggatccccgggtaccgagctcgaa | 14 |
| 11 | tctagagtcgacctgcaggcatgcaa | 15 |
| 12 | gcaggtcgactctagagtggaagccgaagccgaagctac | 16 |
| 13 | tcggtacccggggatccctgcagcttctaaaaagt | 17 |

*The character "h" in the sequences of No. 1 to No. 5 represents "a, c or t," the character "r" represents "g or a," the character "y" represents "c or t," and the character "n" represents inosine.

3. Analysis of Amino Acid Sequence of *Cocos nucifera* L.-Derived Thioesterase

The amino acid sequence of the *Cocos nucifera* L.-derived thioesterase (SEQ ID NO: 1) which is derived from the nucleotide sequence of the CTE gene described above, was analyzed. The identity (homology) of the amino acid sequence was calculated by using a homology analysis (Search homology) program which was based on the Lipman-Pearson method (Science, 227, 1435, (1985)) of a genetic information processing software, Genetyx-Win (Software Development, Inc.), and setting the unit size to compare (ktup) at 2. Furthermore, the alignment between amino acid sequences was produced by using the Clustal W Multiple Alignment Program (Nucleic acids Res. 22, 4673 (1994)) at a default setting.

The sequences of other plant-derived thioesterases and the sequence of the *Cocos nucifera* L.-derived thioesterase described above were compared and analyzed by using the Genetyx-Win. As a result, the *Cocos nucifera* L.-derived thioesterase exhibited an amino acid sequence homology of 50% with a *Umbellularia californica*-derived thioesterase (SEQ ID NO: 3), an amino acid sequence homology of 59% with an *Arabidopsis thaliana*-derived thioesterase (GI: 804947), an amino acid sequence homology of 55% with a *Cuphea*-derived thioesterase (GI: 1292906), an amino acid sequence homology of 49% with a maize-derived thioesterase (GI: 226529781), an amino acid sequence homology of 62% with a palm-derived thioesterase E (GI: 90018255), an amino acid sequence homology of 59% with a rice-derived thioesterase (GI: 125554012), and an amino acid sequence homology of 57% with a soybean-derived thioesterase (GI: 90192131). Thus, it was confirmed that the CTE did not exhibit very high homology with any plant thioesterases (for instance, an *Arabidopsis thaliana*-derived thioesterase exhibited an amino acid sequence homology of 82% with a soybean-derived thioesterase).

The multiple alignment of amino acid sequences of the *Cocos nucifera* L.-derived thioesterase and other plant thioesterases by using the Clustal W Multiple Alignment Program was carried out, and then the amino acid sequence of the *Cocos nucifera* L.-derived thioesterase was compared with that of the *Umbellularia californica*-derived thioesterase. The amino acid sequence of the *Umbellularia californica*-derived thioesterase had the methionine at the $197^{th}$ position (corresponds to the methionine at the $114^{th}$ position in SEQ ID NO: 3), the arginine at the $199^{th}$ position (corresponds to the arginine at the $116^{th}$ position in SEQ ID NO: 3), and the threonine at the $231^{st}$ position (corresponds to the threonine at the $148^{th}$ position in SEQ ID NO: 3), which positions were considered important for the recognition of C12:0 fatty acid as disclosed in the report of Yuan et al. (Proc. Natl. Acad. Sci., USA, Vol. 92, pp. 10639-10643, 1995). As a result, it was found that the methionine at the $197^{th}$ position (corresponds to the methionine at the $117^{th}$ position in SEQ ID NO: 1) and the arginine at the $199^{th}$ position (corresponds to the arginine at the $119^{th}$ position in SEQ ID NO: 1) were conserved in the *Cocos nucifera* L.-derived thioesterase, but the amino acid at the $231^{st}$ position was lysine (corresponds to the lysine at the $151^{st}$ position in SEQ ID NO: 1), which lysine was frequently observed in plant thioesterases other than the *Umbellularia californica*-derived thioesterase. The combination of the methionine at the $197^{th}$ position, the arginine at the $199^{th}$ position, and the lysine at the $231^{st}$ position was also conserved in the thioesterases which principally recognized C16:0 fatty acid, such as the thioesterases of *Arabidopsis thaliana* and maize. For this reason, the recognition of C12:0 fatty acid in the *Cocos nucifera* L.-derived thioesterase may be potentially achieved in a different way from that of the *Umbellularia californica*-derived thioesterase.

As such, the *Cocos nucifera* L.-derived thioesterase of the present invention had relatively low amino acid sequence homology with plant thioesterases that were already known, and the substrate recognitions therebetween were also different.

Example 2

Preparation of Transformant of *Escherichia coli* Having Thioesterase gene

The *Cocos nucifera* L.-derived thioesterase (CTE) gene obtained in Example 1 was introduced into *Escherichia coli* by the technique described below, and thus a transformant was obtained. For a control experiment, a transformant of *Escherichia coli* having the *Umbellularia californica*-derived Acyl-ACP thioesterase (BTE) gene was obtained by the same technique.

1. Construction of Plasmid for CTE Gene Expression

A DNA fragment in which a partial sequence of plasmid vector pMW219 (manufactured by Nippon Gene Co., Ltd.) was applied to both ends of a CTE gene fragment was obtained by a PCR reaction, by using a DNA fragment that encodes the functional part of the *Cocos nucifera* L.-derived thioesterase obtained in Example 1 (SEQ ID NO: 2) as a template, and using the oligo-DNA primers indicated in Table 1 (Primers No. 8 and No. 9 (SEQ ID NO: 12 and SEQ ID NO: 13)). Furthermore, a pMW219 fragment was amplified in a linear form by a PCR reaction, by using pMW219 as a template and using the oligo-DNA primers indicated in Table 1 (Primers No. 10 and No. 11 (SEQ ID NO: 14 and SEQ ID NO: 15)). The CTE gene fragment and the pMW219 fragment were ligated by using an In-Fusion Advantage PCR Cloning Kit (Clontech, Mountain View, Calif.), and thereby, a plasmid which expressed the CTE gene in a form that was fused with the $27^{th}$ amino acid on the N-terminal side of the vector-derived LacZ protein, was constructed.

2. Construction of Plasmid for BTE Gene Expression

A DNA fragment in which a partial sequence of pMW219 was applied to both ends of a BTE gene fragment was obtained by a PCR reaction, by using an a plasmid containing an artificially synthesized DNA fragment that comprises the nucleotide sequence set forth in SEQ ID NO: 4 and that encodes the *Umbellularia californica*-derived thioesterase (BTE), as a template, and using oligo-DNA primers (Table 1, Primers No. 12 and No. 13 (SEQ ID NO: 16 and SEQ ID NO: 17)). Further, the gene comprising the nucleotide sequence set forth in SEQ ID NO: 4 was obtained by the custom synthesis service provided by Invitrogen, Inc. The BTE gene fragment and the pMW219 fragment described above were ligated by using an In-Fusion Advantage PCR Cloning Kit, and thereby, a plasmid which expressed the BTE gene in a form that was fused with the $27^{th}$ amino acid on the N-terminal side of the vector-derived LacZ protein, was constructed.

3. Expression of CTE Gene and BTE Gene in Transformed *Escherichia coli*

*Escherichia coli* mutant strain K27 (fadD88) (Overath et al., Eur. J. Biochem. 7(4): 559-74, 1969, CSCG#: 5478) was transformed by using the CTE gene expression plasmid or the BTE gene expression plasmid constructed as described above. K27 was a variant strain which lacked the fatty acid degradation system. The transformed K27 was left to stand overnight at 30° C., and the colonies thus obtained were inoculated to 1 mL of LBKm liquid medium (Bacto Tripton 1%, Yeast extract 0.5%, NaCl 1%, and kanamycin 50 µg/mL), and the resultant was subjected to shaking culture for 12 hours at 30° C. (preculture). 20 µL of the preculture was inoculated to 2 mL of Overnight Express (trademark) Instant TB medium (Takara Bio, Inc.) containing 50 µg/mL of kanamycin, and was subjected to shaking culture (180 rpm) for 24 hours at 30° C. The turbidity ($OD_{600}$) of the culture at the end of culture was measured. The lipid components contained in the obtained culture medium were analyzed in Example 3.

Example 3

Production of Fatty Acids by Transformed *Escherichia coli*

1. Extraction of Lipid from Transformed *Escherichia coli* and Analysis of Fatty Acid Contained Therein 40 µL of acetic acid, and 40 µL of 7-pentadecanone (0.5 mg/mL) dissolved in methanol as an internal standard were added to 900 µL of the culture medium obtained by Example 2 after a lapse of 24 hours from the initiation of culture. 0.5 mL of chloroform and 1 mL of methanol were added to this liquid, and the mixture was vortexed sufficiently and then was left to stand for 15 minutes. Further, 0.5 mL of a 1.5% aqueous solution of potassium chloride and 0.5 mL of chloroform were added thereto, and the mixture was sufficiently vortexed and then was left to stand for 15 minutes. The mixture was centrifuged at 1,500 rpm for 5 minutes at room temperature, and then the lower layer was collected and dried with nitrogen gas. 1 mL of a boron trifluoride-methanol complex solution was added to the dried sample, and the mixture was kept warm at 80° C. for 10 minutes to thereby performing methyl esterification treatment of fatty acids. Thereafter, 1 mL of saturated saline and 1 mL of hexane were added thereto, and the mixture was sufficiently vortexed and then was left to stand for 30 minutes. The upper layer was collected and provided for gas chromatographic analysis (Hewlett Packard 6890). The gas chromatography was carried out under the conditions as follows: [capillary column: DB-1 MS 30 m×200 µm×0.25 µm (J&W Scientific, Inc.), mobile layer: high purity helium, flow rate inside the column: 1.0 mL/min, temperature rise program: 100° C. (for 1 min)→10° C./min→300° C. (for 5 min), equilibration time: for 1 min, injection port: split injection (split ratio: 100:1), pressure 14.49 psi, 104 mL/min, amount of injection 1 µL, vial cleaning: methanol.chloroform, detector temperature: 300° C.].

2. Analysis of Fatty Acid Content

Amounts of fatty acid methyl esters were quantitatively determined based on the peak areas of the waveform data obtained by the above gas chromatographic analysis. The peak areas corresponding to the individual fatty acids were compared with that of 7-pentadecanone as the internal standard, and carried out corrections between the samples, and then the contents of the individual fatty acids per liter of the culture medium were calculated. Further, the contents of the individual fatty acids calculated above were normalized with respect to the previously measured value of the light absorbance (OD600) of the culture medium at the end of culture. The results are shown in FIG. 1.

Furthermore, the total content of the individual fatty acids was calculated by summing the contents of the individual fatty acids described above. The results are shown in FIG. 2.

As is obvious from FIG. 1, in the transformant having the *Cocos nucifera* L.-derived thioesterase introduced therein, lauric acid (C12:0), myristic acid (C14:0) and palmitoleic acid (C16:1) were primarily accumulated. The amount of accumulation of lauric acid (C12:0) was approximately equal to or greater than the amount of accumulation in the transformant having the *Umbellularia californica*-derived thioesterase (BTE) introduced therein.

Figure 2:
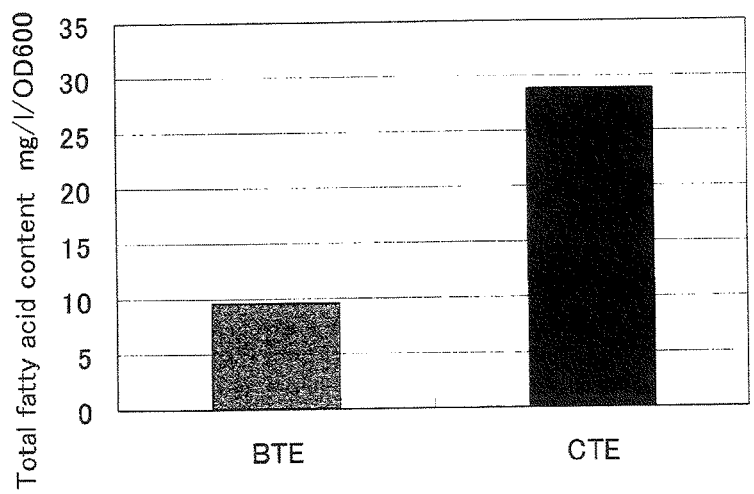
{FIG. 2}

Furthermore, as is obvious from FIG. 2, the transformant having the *Cocos nucifera* L.-derived thioesterase introduced therein showed about 3 times amount of a total fatty acid compared to that of the transformant having the *Umbellularia californica*-derived thioesterase (BTE) introduced therein. Thus, it was confirmed that the productivity for fatty acids and lipids had been enhanced to a large extent in the transformant having the *Cocos nucifera* L.-derived thioesterase introduced therein.

3. Collection of Lipids in *Cocos nucifera* L. Endosperm and Analysis of Fatty Acid Composition 0.5 mL of chloroform, 0.5 mL of methanol, and 0.25 mL of a 1.5% aqueous solution of potassium chloride were added to about 100 mg of the *Cocos nucifera* L. endosperm, and the mixture was vortexed. 40 µL of acetic acid and 40 µL of 7-pentadecanone dissolved in methanol (0.5 mg/mL) were further added to the mixture. 0.5 mL of chloroform and 1 mL of methanol were added thereto, and thereafter, the operation was carried out in the same manner as in Section 1 described above. Thus, collection of fatty acids and an analysis of fatty acids were carried out.

Amounts of fatty acid methyl esters were quantitatively determined based on the peak areas of the waveform data obtained by the gas chromatographic analysis. The fatty acid composition ratio was calculated based on the peak areas. The results are shown in FIG. 3.

Figure 3:
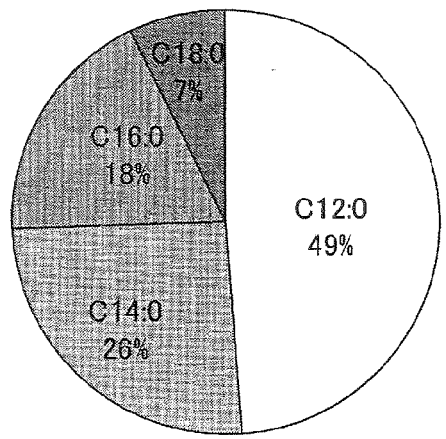
{FIG. 3}
Figure 3:
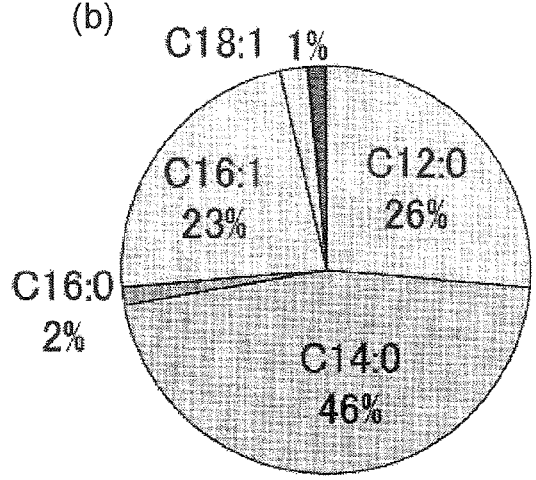

As is obvious from FIG. 3, in the *Cocos nucifera* L. endosperm, lauric acid (C12:0) was accumulated to the greatest extent and fatty acids were accumulated in the order of myristic acid (C14:0), palmitic acid (C16:0), and stearic acid (C18:0).

On the other hand, in the transformant having the *Cocos nucifera* L.-derived thioesterase introduced therein, myristic acid (C14:0) was accumulated to the greatest extent, and lauric acid (C12:0) was accumulated to the second greatest extent. Furthermore, palmitoleic acid (C16:1), the accumulation of which is hardly observed in the endosperm, was accumulated to an equal extent with lauric acid (C12:0). From the results, it was found that when the *Cocos nucifera* L.-derived thioesterase of the present invention was used, fatty acids of a composition that was different from the fatty acid composition of the *Cocos nucifera* L. endosperm could be produced in the transformant.

Example 4

Construction of Transformant by Introducing Thioesterase Gene into *Arabidopsis thaliana*

The *Cocos nucifera* L.-derived thioesterase (CTE) gene obtained in Example 1 was introduced into *Arabidopsis thaliana* by the techniques described below, and thus a transformant was produced.
1. Construction Plasmid for CTE Gene Expression in *Arabidopsis Thaliana*
(1) Cloning of Promoter Region and Terminator Region of *Napin* Gene A promoter region of *Napin* gene derived from *Brassica rapa* was obtained by using a wild oilseed rape-like plant collected from Itako City, Ibaraki Prefecture, and a terminator region of *Napin* gene derived from *Brassica rapa* was obtained by using a wild oilseed rape-like plant collected from Mashiko-cho, Tochigi Prefecture, respectively according to the following method.

Genome DNAs were extracted from the plants described above using Power Plant DNA Isolation Kit (MO BIO Laboratories, USA). The promoter and terminator regions were amplified by PCR using the genome DNA as a template and a DNA polymerase PrimeSTAR. Specifically, the promoter region of *Napin* gene derived from *Brassica rapa* was amplified by using a pair of Primers No. 1 and No. 2 (SEQ ID NO: 21 and SEQ ID NO: 22) as shown in Table 2, and the terminator region of *Napin* gene derived from *Brassica rapa* was amplified by using a pair of Primers No. 3 and No. 4 (SEQ ID NO: 23 and SEQ ID NO: 24). Further, PCR was carried out again using the PCR products of the amplified promoter and terminator of *Napin* gene derived from *Brassica rapa*, as templates. At this PCR, a pair of Primers No. 5 and No. 6 (SEQ ID NO: 25 and SEQ ID NO: 26) as shown in Table 2 was used for amplifying the promoter of *Napin* gene, and a pair of Primers No. 3 and No. 7 (SEQ ID NO: 23 and SEQ ID NO: 27) as shown in Table 2 was used for amplifying the terminator of *Napin* gene. The DNA fragments amplified by PCR were treated by adding deoxyadenine (dA) to the two ends of the fragment using Mighty TA-cloning Kit (manufactured by Takara Bio, Inc.), and subsequently the DNA fragments were respectively inserted into pMD20-T vector (manufactured by Takara Bio, Inc.) by ligation. As a result, a plasmid pPNapin1 containing the *Napin* gene promoter and a plasmid pTNapin1 containing the *Napin* gene terminator were respectively constructed. These plasmids were supplied to sequence analysis, and thus the nucleotide sequence of the promoter region (SEQ ID NO: 18) and the nucleotide sequence of the terminator region (SEQ ID NO: 19) were determined.
(2) Construction of Vector for Transfection of Plant Cell As a vector for transfection of plant cells, pRI909 (manufactured by Takara Bio, Inc.) was used.

First, the promoter and the terminator of *Napin* gene derived from *Brassica rapa* were introduced into pRI909. A DNA fragment of the promoter region in which a restriction-enzyme recognition sequence was added to both ends of the fragment, was amplified by PCR using PrimeSTAR with the plasmid pPNapin1 produced in the above section (1) as a template, and a pair of Primers No. 8 and No. 9 (SEQ ID NO: 28 and SEQ ID NO: 29) as shown in Table 2. Further, a DNA fragment of the terminator region was amplified by PCR using PrimeSTAR with the plasmid pTNapin1 as a template, and a pair of Primers No. 10 and No. 11 (SEQ ID NO: 30 and SEQ ID NO: 31) as shown in Table 2. The amplified fragments were treated by adding deoxyadenine (dA) to the two ends of the fragment using Mighty TA-cloning Kit (manufactured by Takara Bio, Inc.), and subsequently the fragments were respectively inserted into pMD20-T vector (manufactured by Takara Bio, Inc.) by ligation, and thus plasmids pPNapin2 and pTNapin2 were respectively constructed. The plasmid pPNapin2 was treated with restriction enzymes Sal I and Not I, and the plasmid pTNapin2 was treated with restriction enzymes Sma I and Not I. The treated plasmids were inserted into pRI909 (that was previously treated with restriction enzymes Sal I and Sma I) by ligation, and thus, plasmid p909PTnapin was constructed.

A gene encoding the chloroplast transit signal peptide of the Acyl-ACP thioesterase (BTE) gene derived from *Umbellularia californica* was obtained by utilizing the custom synthesis service provided by Invitrogen, Inc. (Carlsbad, Calif.) (SEQ ID NO: 20).

A plasmid containing a sequence of the gene obtained above was used as a template, and a gene fragment that encodes the chloroplast transit signal peptide was amplified by PCR using PrimeSTAR and a pair of Primers No. 12 and No. 13 (SEQ ID NO: 32 and SEQ ID NO: 33) as shown in Table 2. The amplified gene fragments were treated by adding deoxyadenine (dA) to the two ends of the fragment using Mighty TA-cloning Kit (manufactured by Takara Bio, Inc.), and subsequently the gene fragments were respectively inserted into pMD20-T vector (manufactured by Takara Bio, Inc.) by ligation. As a result, a plasmid pSignal was constructed. The plasmid pSignal was digested with restriction enzyme Not I, and the digestion fragments were linked into Not I site of p909PTnapin a by ligation. As a result, a plasmid p909PTnapin-S was constructed.

A DNA fragment encoding the CTE gene was amplified by a PCR reaction, by using a gene that encodes the functional part of the *Cocos nucifera* L.-derived thioesterase (CTE) obtained in Example 1 (SEQ ID NO: 2) as a template, and using PrimeSTAR MAX and a pair of Primers No. 14 and No. 15 (SEQ ID NO: 34 and SEQ ID NO: 35) indicated in Table 2. Furthermore, p909PTnapin-S was amplified as a linear fragment, by using p909PTnapin-S as a template, and using a pair of Primers No. 16 and No. 17 (SEQ ID NO: 36 and SEQ ID NO: 37). The CTE gene fragment and the p909PTnapin-S fragment were ligated by using an In-Fusion Advantage PCR Cloning Kit (manufactured by Clontech Laboratories, Inc.)

Thus, a plasmid for transfection of plant, p909CTE, containing the *Cocos nucifera* L.-derived thioesterase (CTE) gene sequence was constructed. In this plasmid, the expression of the CTE was controlled by the *Brassica rapa* (canola)-derived *Napin* gene promoter, and the CTE was transferred to chloroplasts by the chloroplast transit signal peptide derived from the *Umbellularia californica*-derived thioesterase gene (BTE).

*dopsis thaliana*, an analysis of the lipid content and the fatty acid composition in the seeds was carried out by the techniques described below.

1. Lipid Extraction from Seeds and Methyl Esterification of Fatty Acids

Approximately two spoons of the *Arabidopsis thaliana* seeds harvested above were corrected with a seed spoon (200-grain capacity, manufactured by Biomedical Science Co., Ltd.) and were put into Lysing Matrix D (MP Biomedicals, Inc., USA). The Lysing Matrix D was mounted on FastPrep

TABLE 2

Table 2

| Primer No. | Sequence (5'-3') | SEQ ID NO. |
| --- | --- | --- |
| 1 | GATATCACTACAATGTCGGAGAGACAAGGC | 21 |
| 2 | TTGTGTATGTTCTGTAGTGATGAGTTTTGG | 22 |
| 3 | AGTGTGTATACCACGGTGATATGAGTGT | 23 |
| 4 | AAGCTTTATCGGTAAAACAACGAGCAGAG | 24 |
| 5 | GGGGGTCGACGATATCACTACAATGTCGGAGAGACAAGGCTGCGCCA | 25 |
| 6 | GCTAAAGAGGTGGTGGCCATTTGTGTATGTTCTGTAGTGATGAGTTTTGGTTTGAGT | 26 |
| 7 | CCCCCCGGGAAGCTTTATCGGTAAAACAACGAGCAGAGCAAGAAT | 27 |
| 8 | GGGGGTCGACGATATCACTACAATGTCGGAGAGACAAGGCTGCGCCA | 28 |
| 9 | CATATGCCGCGGCCGCCCACTAGTTTGTGTATGTTCTGTAGTGATGAGTT | 29 |
| 10 | ACTAGTGGGCGGCCGCGGCATATGGTGTGTATACCACGGTGATATGAGT | 30 |
| 11 | CCCCCCGGGAAGCTTTATCGGTAAAACAACGAGCAGAGCAAGAAT | 31 |
| 12 | GCGGCCGCATGGCCACCACCTCTTTAGCTT | 32 |
| 13 | GCGGCCGCTCTAGATTGGTCCACTGCTTCTCAGCAGCCG | 33 |
| 14 | TGGACCAATCTAGAGCTCGATTCCAAGAAGAGGGGGG | 34 |
| 15 | ATATGCCGCGGCCGCTCATTTACTCTCAGTTGGGTGC | 35 |
| 16 | CTCTAGATTGGTCCACTGCTTCTCA | 36 |
| 17 | GCGGCCGCGGCATATGGTGTGTA | 37 |

2. Method of Transformation and Growth of *Arabidopsis thaliana*

The vector p909CTE for transfection of plant was supplied to the custom service for *Arabidopsis thaliana* transformation by Inplanta Innovations, Inc., and thus a transformant of *Arabidopsis thaliana* (Colombia) having the CTE gene introduced therein. Pnapin-CTE, was obtained.

The wild-type strain of *Arabidopsis thaliana* and the transformants Pnapin-CTE were grown in the soil at room temperature of 22° C., under the conditions of a light period of 16 hours (about 4000 lux) using fluorescent lamp illumination and a dark period of 8 hours. After the cultivation for about 2 months, seeds were harvested.

Example 5

Production of Fatty Acids and Lipids in *Arabidopsis thaliana* Transformant

For the *Arabidopsis thaliana* transformant (Pnapin-CTE) constructed in Example 4 and the wild-type strain of *Arabi*-

(MP Blomedicals LLC), and the seeds were crushed by applying vibration for 20 seconds at a speed of 6.0. 20 µL of 7-pentadecanone (0.5 mg/mL methanol) (internal standard) and 20 µL of acetic acid were added to the crushed seeds. 0.25 mL of chloroform and 0.5 mL of methanol were added thereto, and the mixture was sufficiently vortexed and then was left to stand for 15 minutes. Further, 0.25 mL of a 1.5% aqueous solution of potassium chloride and 0.25 mL of chloroform were added thereto, and the mixture was sufficiently vortexed and then was left to stand for 15 minutes. The mixture was centrifuged at 1,500 rpm for 5 minutes at room temperature, and then the lower layer was collected and dried with nitrogen gas. 100 µL of 0.5 N KOH-methanol solution was added to the dried samples, and the mixture was kept at a constant temperature of 70° C. for 30 minutes to hydrolyze triacylglycerol. The dried product was dissolved by adding 0.3 mL of a boron trifluoride-methanol complex solution, and the solution was kept at a constant temperature of 80° C. for 10 minutes to thereby carry out methyl esterification of fatty acids. Thereafter, 0.2 mL of saturated saline and 0.3 mL of hexane were added thereto, and the mixture was sufficiently vortexed and then was left to stand for 30 minutes. The hexane layer (upper layer) containing methyl esters of fatty acids was collected and supplied to gas chromatographic (GC) analysis.

2. Gas Chromatographic (GC) Analysis

The methyl-esterified samples obtained above were analyzed by Gas chromatography (GC). The GC was carried out using column: DB1-MS (J&W Scientific, Inc., Folsom, Calif.) and analysis apparatus: 6890 (Agilent Technologies, Inc., Santa Clara, Calif.), under the conditions as follows: [column oven temperature: maintained for 1 min at 100° C.→100° C. to 300° C. (temperature increase at 10° C./min) →maintained for 5 min at 300° C. (post-run for 2 min), injection port detector temperature: 300° C., injection method: split mode (split ratio=193:1), amount of sample injection 1 μL to 2 μL, column flow rate: constant at 0.5 mL/min, detector: FID, carrier gas: hydrogen, makeup gas: helium]. Amounts of fatty acid methyl esters were quantitatively determined based on the peak areas of the waveform data obtained by the GC analysis. The peak areas corresponding to the individual fatty acids were compared with that of 7-pentadecanone as the internal standard, and carried out corrections between the samples, and then the contents of the individual fatty acids in the whole seeds supplied to the analysis were calculated. Further, the contents of the individual fatty acids per 100 seeds were calculated by dividing the calculated fatty acid contents by the number of seeds previously measured. Meanwhile, the peak of GC corresponding to the individual fatty acid in the seeds was identified by the retention time (RT) of a methyl ester of a standard product of the individual fatty acid, and by the analysis by GC/MS described below.

3. GC/MS Analysis

The samples after the GC analysis were supplied to GC/Mass Spectrometric (MS) analysis, if needed. The GC/MS analysis was carried out using capillary column: DB1-MS. GC analysis apparatus: 7890A (Agilent Technologies, Inc.), and MS analysis apparatus: 5975C (Agilent Technologies, Inc.) under the following conditions: [column oven temperature: maintained for 2 min at 100° C.→100° C. to 300° C. (temperature increase at 10° C./min)→maintained for 5 min at 300° C. (equilibration time 2 min, post-run for 5 min at 320° C.) or maintained for 2 min at 100° C.→100° C. to 200° C. (temperature increase 10° C./min)→200° C. to 320° C. (temperature increase 50° C./min)→maintained for 5 min at 320° C. (equilibration time 2 min, post-run for 5 min at 320° C.), injection port detector temperature: 250° C., injection method: splitless mode, amount of sample injection: 1 μL, column flow rate: constant at 1 mL/min, detector: FID, carrier gas: hydrogen, makeup gas: helium, solvent retention time: 7 min or 3.5 min, ionization method: El method, ion source temperature: 250° C., interface temperature: 300° C., measurement mode: scan mode (m/z: 20 to 550 or 10 to 550)].

Figure 4:
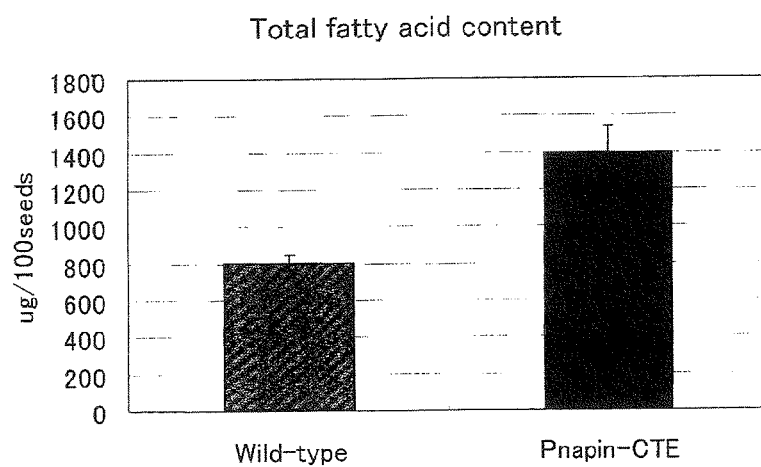
{FIG. 4 }
Figure 5:
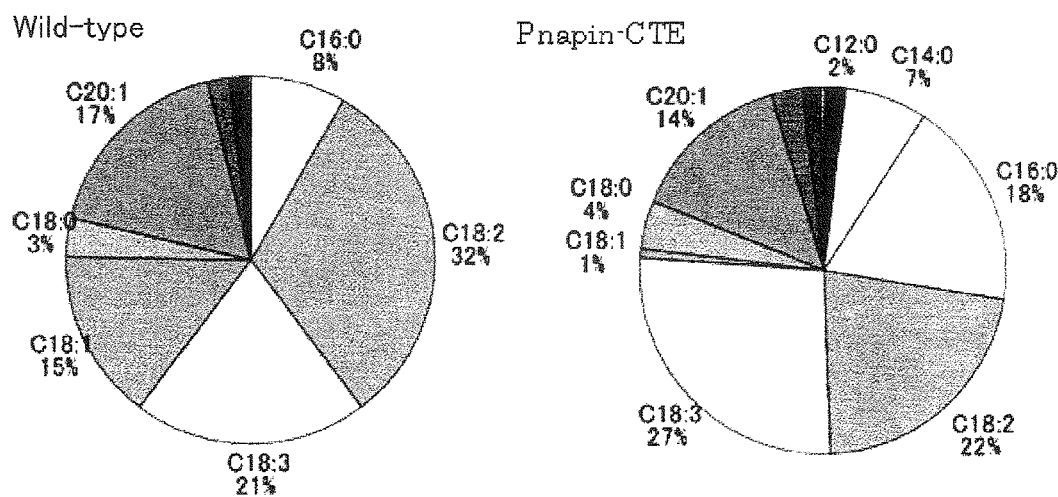
{FIG. 5 }

Based on the peak areas of the waveform data obtained by the GC analysis, the contents of the individual fatty acids in the seeds of the *Arabidopsis thaliana* transformant (Pnapin-CTE) or the wild-type strain of *Arabidopsis thaliana*, were calculated. FIG. 4 shows the total fatty acid content (the total lipid content), and FIG. 5 shows the proportions of individual fatty acids in the total fatty acid content. Further, in FIGS. 4 and 5, the lipid content of the wild-type strain seeds means the average value of the results obtained from two independent groups of seeds, and the lipid content of the transformant Pnapin-CTE means the average value of five independent lines.

As is apparent from FIG. 4, total fatty acid content (the lipid content) of the seeds harvested from the transformant Pnapin-CTE having the CTE gene is larger than that of the seeds harvested from the wild strain of *Arabidopsis thaliana*.

Furthermore, as is apparent from FIG. 5, the transformant Pnapin-CTE contained lauric acid (C12:0) and myristic acid (C14:0) that were not contained in wild-type *Arabidopsis thaliana*, and even the amount of palmitic acid (C16:0) was increased. Furthermore, the transformant Pnapin-CTE contained larger amounts of myristic acid (C14:0) and palmitic acid (C16:0) than lauric acid (C12:0), and thus, it was understood that the fatty acid composition of the transformant was different from the fatty acid composition of the *Cocos nucifera* L. endosperm.

Therefore, it was found that the productivity for fatty acids and lipids of a transformant could be enhanced by the *Cocos nucifera* L.-derived thioesterase of the present invention, and fatty acids could be produced at proportions that are different from the fatty acid composition of the *Cocos nucifera* L. endosperm.

Industrial Applicability

The thioesterase of the present invention has the excellent productivity of fatty acids. The productivity for fatty acids and lipids of a transformant obtained by introducing a gene encoding the thioesterase into a microorganism, a plant or the like, can be increased. Fatty acids, lipids and derivatives thereof produced by the transformant can be utilized for food, an emulsifier for cosmetic products and the like, a cleansing agent such as a soap or a detergent, a fiber treatment agent, a hair conditioning agent, a disinfectant, an antiseptic, and the like.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2010-106570 filed in Japan on May 6, 2010, and Patent Application No. 2011-20737 filed in Japan on Feb. 2, 2011, each of which is entirely herein incorporated by reference.

The invention claimed is:

1. A recombinant vector comprising an isolated cDNA, the isolated cDNA comprising any one of the following DNAs (a) to (f):
   (a) DNA encoding a protein that comprises an amino acid sequence set forth in SEQ ID NO: 1, wherein said protein has thioesterase activity,
   (b) DNA encoding a protein that comprises an amino acid sequence in which one to two amino acids are deleted, substituted, inserted and/or added in the amino acid sequence set forth in SEQ ID NO: 1, wherein said protein has thioesterase activity,
   (c) DNA encoding a protein that comprises an amino acid sequence having at least 90% sequence identity to the amino acid sequence set forth in SEQ ID NO: 1, wherein said protein has thioesterase activity;
   (d) DNA comprising the nucleotide sequence set forth in SEQ ID NO: 2, which codes for a protein having thioesterase activity,
   (e) DNA capable of hybridizing with a DNA comprising a complementary sequence to the nucleotide sequence set forth in SEQ ID NO: 2 when incubated in a solution containing 6 x SSC, 0.5% SDS, 5x Denhardt and 100 mg/mL herring sperm DNA at 65° C. for 8 to 16 hours, and which codes for a protein having thioesterase activity, and
   (f) DNA comprising a nucleotide sequence having at least 90% sequence identity to the nucleotide sequence set forth in SEQ ID NO: 2, which codes for a protein having thioesterase activity.

2. The recombinant vector of claim 1, wherein said gene is said
   (d) A DNA comprising the nucleotide sequence set forth in SEQ ID NO: 2, which codes a protein having thioesterase activity,
   (e) A DNA capable of hybridizing with a DNA comprising a complementary sequence to the nucleotide sequence set forth in SEQ ID NO: 2 when incubated in a solution containing 6 x SSC, 0.5% SDS, 5x Denhardt and 100 mg/mL herring sperm DNA at 65° C. for 8 to 16 hours, and which codes a protein having thioesterase activity, or
   (f) A DNA comprising a nucleotide sequence having at least 90% sequence identity to the nucleotide sequence set forth in SEQ ID NO: 2, which codes a protein having thioesterase activity.

3. The recombinant vector of claim 2, in which the DNA comprises the nucleotide sequence set forth in SEQ ID NO: 2.

4. A transformant that has been transformed with DNA or with a recombinant vector, said DNA or said recombinant vector comprising
   (a) A cDNA encoding a protein that comprises the amino acid sequence set forth in SEQ ID NO: 1, wherein said protein has thioesterase activity,
   (b) A cDNA encoding a protein that comprises an amino acid sequence in which one to two amino acids are deleted, substituted, inserted and/or added in the amino acid sequence set forth in SEQ ID NO: 1, wherein said protein has thioesterase activity,
   (c) A cDNA encoding a protein that comprises an amino acid sequence having at least 90% sequence identity to the amino acid sequence set forth in SEQ ID NO: 1, wherein said protein has thioesterase activity,
   (d) A DNA comprising the nucleotide sequence set forth in SEQ ID NO: 2, which codes a protein having thioesterase activity,
   (e) A DNA capable of hybridizing with a DNA comprising a complementary sequence to the nucleotide sequence set forth in SEQ ID NO: 2 when incubated in a solution containing 6 x SSC, 0.5% SDS, 5x Denhardt and 100 mg/mL herring sperm DNA at 65° C. for 8 to 16 hours, and which codes a protein having thioesterase activity, and (f) A DNA comprising a nucleotide sequence having at least 90% sequence identity to the nucleotide sequence set forth in SEQ ID NO: 2, which codes a protein having thioesterase activity.

5. The transformant according to claim 4, wherein said transformant is a microorganism.

6. The transformant according to claim 5, wherein said microorganism is *Escherichia coli*.

7. The transformant according to claim 4, wherein said transformant is a plant.

8. A method of producing a fatty acid, comprising culturing the transformant according to claim 4 in a culture medium, and collecting said fatty acid from the culture of the medium.

9. A method of producing a lipid containing a fatty acid, comprising culturing the transformant according to claim 4 in a culture medium, and collecting said lipid containing said fatty acid from the culture of the medium.

10. The method according to claim 8, wherein the fatty acid is a long-chain fatty acid having 12 or more carbon atoms.

11. The method according to claim 10, wherein the fatty acid is at least one fatty acid selected from the group consisting of lauric acid, myristic acid, palmitic acid and palmitoleic acid.

12. A method of enhancing productivity of a fatty acid or a lipid containing a fatty acid, comprising introducing a cDNA that comprises any one of the following (a) to (f) into a host:

(a) A cDNA that encodes a protein that comprises the amino acid sequence set forth in SEQ ID NO: 1, wherein said protein has thioesterase activity, (b) A cDNA that encodes a protein that comprises an amino acid sequence in which one to two amino acids are deleted, substituted, inserted and/or added in the amino acid sequence set forth in SEQ ID NO: 1, wherein said protein has thioesterase activity, (c) A cDNA that encodes a protein that comprises an amino acid sequence having at least 90% sequence identity to the amino acid sequence set forth in SEQ ID NO: 1, wherein said protein has thioesterase activity, (d) A DNA comprising a nucleotide sequence set forth in SEQ ID NO: 2, which codes a protein having thioesterase activity, (e) A DNA capable of hybridizing with a DNA comprising a complementary sequence to the nucleotide sequence set forth in SEQ ID NO: 2 when incubated in a solution containing 6 x SSC, 0.5% SDS, 5x Denhardt and 100 mg/mL herring sperm DNA at 65° C. for 8 to 16 hours, and which codes a protein having thioesterase activity, and (f) A DNA comprising a nucleotide sequence having at least 90% sequence identity to the nucleotide sequence set forth in SEQ ID NO: 2, which codes a protein having thioesterase activity.

13. The transformant according to claim 7, wherein said plant is *Arabidopsis thaliana*.

14. The method of producing a lipid containing a fatty acid according to claim 9, wherein the fatty acid is a long-chain fatty acid having 12 or more carbon atoms.

15. The method of producing a lipid containing a fatty acid according to claim 14, wherein the fatty acid is at least one fatty acid selected from the group consisting of lauric acid, myristic acid, palmitic acid and palmitoleic acid.

* * * * *